United States Patent
Bouchemal et al.

(10) Patent No.: US 10,172,947 B2
(45) Date of Patent: Jan. 8, 2019

(54) ANTIPARASITIC AND/OR ANTIFUNGAL COMPOSITION COMPRISING HYDROPHOBISED CHITOSAN

(71) Applicants: CENTRE NATIONAL DE LA RECHERCHE SCIENTIFIQUE (CNRS), Paris (FR); UNIVERSITE PARIS-SUD 11, Orsay (FR)

(72) Inventors: Kawthar Bouchemal, Palaiseau (FR); Christian Bories, Saint Maur des Fosses (FR); Philippe Loiseau, Gif sur Yvette (FR); Christine Vauthier-Holtzscherer, Gif sur Yvette (FR); Sebastien Pomel, Les Ulis (FR); Benedicte Pradines, Chatenay-Malabry (FR)

(73) Assignees: CENTRE NATIONAL DE LA RECHERCHE SCIENTIFIFQUE (CNRS), Paris (FR); UNIVERSITE PARIS-SUD 11, Orsay (FR)

( * ) Notice: Subject to any disclaimer, the term of this patent is extended or adjusted under 35 U.S.C. 154(b) by 0 days.

(21) Appl. No.: 15/027,147

(22) PCT Filed: Oct. 9, 2014

(86) PCT No.: PCT/FR2014/052569
§ 371 (c)(1),
(2) Date: Apr. 4, 2016

(87) PCT Pub. No.: WO2015/052448
PCT Pub. Date: Apr. 16, 2015

(65) Prior Publication Data
US 2016/0243243 A1 Aug. 25, 2016

(30) Foreign Application Priority Data
Oct. 9, 2013 (FR) ...................................... 13 59777

(51) Int. Cl.
| | | |
|---|---|---|
| *A61K 47/36* | (2006.01) | |
| *A61K 47/40* | (2006.01) | |
| *A61K 31/155* | (2006.01) | |
| *A61K 31/7048* | (2006.01) | |
| *A61K 47/69* | (2017.01) | |

(52) U.S. Cl.
CPC ............ *A61K 47/36* (2013.01); *A61K 31/155* (2013.01); *A61K 31/7048* (2013.01); *A61K 47/40* (2013.01); *A61K 47/6939* (2017.08); *A61K 47/6951* (2017.08)

(58) Field of Classification Search
CPC .. A61K 31/155; A61K 31/7048; A61K 47/36; A61K 47/40; A61K 47/48923; A61K 47/48969
See application file for complete search history.

(56) References Cited

U.S. PATENT DOCUMENTS

| 4,363,760 A | 12/1982 | Cioca |
| 4,659,740 A | 4/1987 | Usher |
| 5,679,657 A | 10/1997 | Oka et al. |
| 6,703,490 B1 | 3/2004 | Perrier et al. |
| 7,682,635 B2 * | 3/2010 | Gref ..................... A61K 9/5161 424/499 |
| 2002/0143171 A1 | 10/2002 | Yui et al. |
| 2008/0220030 A1* | 9/2008 | Alonso Fernandez ...................... A61K 9/0043 424/401 |
| 2010/0098794 A1 | 4/2010 | Armand |
| 2011/0223151 A1 | 9/2011 | Behrens et al. |
| 2015/0151005 A1* | 6/2015 | Bouchemal ........ A61K 47/4823 424/489 |

FOREIGN PATENT DOCUMENTS

| FR | 2739860 A1 | 4/1997 |
| JP | 2003267817 A | 9/2003 |
| JP | 2007 191396 A | 8/2007 |
| KR | 20150015209 | 2/2015 |
| RU | 2 383 341 C2 | 3/2010 |
| RU | 2 524 663 C1 | 7/2014 |
| TW | 201343190 A | 11/2013 |
| WO | 2005116085 A1 | 12/2005 |
| WO | 2006107825 A2 | 10/2006 |
| WO | 2008003685 A1 | 1/2008 |
| WO | 2013150193 A1 | 10/2013 |

OTHER PUBLICATIONS

Kambiz Gilani et al. (Journal of Pharmaceutical Sciences, vol. 100, No. 1, Jan. 2011).*
Tiyaboonchai W. et al. (Int J Pharm Feb. 1, 2007, 329(1-2)142-9).*
Bertholon et al. (Langumuir 2006, 22, 5485-5490.*
Burckbuchler, Virginie, et al. "Rheological and structural characterization of the interactions between cyclodextrin compounds and hydrophobically modified alginate." Biomacromolecules 7.6 (2006): 1871-1878, 1871 (left column).*
Bouchemal et al. (J. Drug Del. Sci. Tech., 18 (6) 392-397 2008).*
Bertholon et al. (Macromolecules 2006, 39, 3559-3567).*
Vieira, D.B. et al. "Cationic nanoparticles for delivery of amphotericin B: preparation, characterization and activity in vitro." J. Nanobiotech., Jan. 2008, 6:6.

(Continued)

*Primary Examiner* — Anna R Falkowitz
(74) *Attorney, Agent, or Firm* — Young & Thompson

(57) ABSTRACT

A composition including hydrophobized chitosan can be used as an antiparasitic and/or antifungal agent or in the treatment of parasitic and/or fungal infections. The composition may include an antifungal agent and hydrophobized chitosan. The antifungal agent can be in association with the hydrophobized chitosan, with the latter being more preferably in the particle form, or the antifungal agent can be encapsulated in particles including the hydrophobized chitosan. The use of the composition as an antifungal agent or in the treatment of fungal infections, and a method for manufacturing the composition are also described.

20 Claims, 7 Drawing Sheets

(56) References Cited

OTHER PUBLICATIONS

Albasarah et al. "Chitosan-coated antifungal formulations for nebulisation." J. Pharmacy Pharmacol., vol. 62, No. 7, Jul. 2010, pp. 821-828.
Gharib, A. et al. "Preparation and antifungal activity of spray-dried amphotericin B-loaded nanospheres." DARU, vol. 19, No. 5, 2011, pp. 351-355.
Odds, F.C. "Synergy, antagonism, and what the chequerboard puts between them." J. Antimicrobial Chemotherapy, vol. 52, No. 1, Jul. 2003.
Huang, M. et al. "Uptake and cytotoxicity of chitosan molecules and nanoparticles: effects of molecular weight and degree of deacetylation." Pharmaceutical Research, vol. 21, No. 2, Feb. 2004, pp. 344-353.
Bemkop-Schnürch, A. et al. "Thiolated polymers-thiomers: synthesis and in vitro evaluation of chitosan-2-iminothiolane conjugates." International Journal of Pharmaceutics, vol. 260, No. 2, Jul. 2003, pp. 229-237.
Bravo-Osuna, I. et al. "Mucoadhesion mechanism of chitosan and thiolated chitosan-poly(isobutyl cyanoacrylate) core-shell nanoparticles." Biomaterials, vol. 28, No. 13, Apr. 2007, pp. 2233-2243.
Chauvierre, C. et al. "Radical emulsion polymerization of alkylcyanoacrylates initiated by the redox system dextran-cerium (IV) under acidic aqueous conditions." Macromolecules, 2003, vol. 36, No. 16, pp. 6018-6027.
Bravo-Osuna, I. et al. "Elaboration and characterization of thiolated chitosan-coated acrylic nanoparticles." Int. J. Pharm, vol. 316, Issues 1-2, Apr. 2006, pp. 170-175.
Gilani, V. et al. "Development of respirable nanomicelle carriers for delivery of amphotericin B by jet nebulization." J. Pharm. Sciences, vol. 100, No. 1, Jan. 2011, pp. 252-259.
Moazeni, E. et al. "Preparation and evaluation of inhalable itraconazole chitosan based polymeric micelles." DARU Journal of Pharmaceutical Sciences, vol. 20, No. 85, Dec. 2012, pp. 1-9.
Song, S. et al. "Self-aggregated nanoparticles based on amphiphilic poly(lactic acid)-grafted-chitosan copolymer for ocular delivery of amphotericin B." Int. J. Nanomedicine, Sep. 2013, pp. 3715-3728.
Siew et al. "Enhanced oral absorption of hydrophobic and hydrophilic drugs using quaternary ammonium palmitoyl glycol chitosan nanoparticles." Molecular Pharmaceutics, vol. 9, No. 1, Jan. 2012, pp. 14-28.
Saint-Pierre-Chazalet, M. et al. "Membrane sterol depletion impairs miltefosine action in wild-type and miltefosine-resistant Leishmania donovani promastigotes." J. Antimicrob. Chemother., Nov. 2009, vol. 64, No. 5, pp. 993-1001.
Audisio, D. et al. "Synthesis and antikinetoplastid activities of 3-substituted quinolinones derivatives." Eur. J. Med. Chem., Jun. 2012, vol. 52, pp. 44-50.
Owen, D.H. and Katz, D.F. "A vaginal fluid stimulant." Contraception, Feb. 1999, vol. 59, No. 2, pp. 91-95.
Camuzat-Dedenis, B. et al. "Synthesis and in vitro trichomonacidal activities of some new dialkylperoxides and 1,2,4-trioxanes." Eur. J. Med. Chem., vol. 36, No. 10, Oct. 2001, pp. 837-842.
Mannila et al. "Cyclodextrins and chitosan derivatives in sublingual delivery of low solubility peptides: A study using cyclosprin A, alpha-cyclodextrin and quaternary chitosan N-betainate." International Journal of Pharmaceutics, vol. 381, No. 1, Oct. 2009, pp. 19-24.
Huh, K.M. et al. "Supramolecular hydrogel formation based on inclusion complexation between PEG-modified chitosan and alpha-cyclodextrin." Macromolecular Bioscience, Feb. 2004, vol. 4, No. 2, pp. 92-99.
Rinaudo, M. et al. "Specific interactions in modified chitosan systems." Biomacromolecules, vol. 6, No. 5, Sep. 2005, pp. 2396-2407.
Desbrieres, J. et al. "Hydrophobic derivatives of chitosan: characterization and rheological behavior." International Journal of Biological Macromolecules, Elsevier, Jan. 1996, vol. 19, No. 1, pp. 21-28.
Galant, C. et al. "Altering associations in aqueous solutions of a hydrophobically modified alginate in the presence of beta-cyclodextrin monomers." The Journal of Physical Chemistry B, Jan. 2006, vol. 110, No. 1, pp. 190-195.
Burckbuchler, V. et al. "Rheological and structural characterization of the interactions between cyclodextrin compounds and hydrophobically modified alginate." Biomacromolecules, Jun. 2006, vol. 7, No. 6, pp. 1871-1878.
Dowling, M.B. et al. "A self-assembling hydrophobically modified chitosan capable of reversible hemostatic action." Biomaterials Elsevier Science, May 2011, vol. 32, No. 13, pp. 3351-3357.
Karlberg, M. et al. "Gels of hydrophobically modified hydroxyethyl cellulose cross-linked by amylose. Competition with cyclodextrin", The ACS Journal of Surfaces and Colloids, Feb. 2006, vol. 22, No. 5, pp. 2241-2248.
Sashiwa et al. "Chemical modification of chitosan. 13. Synthesis of organosoluble, palladium adsorbable, and biodegradable chitosan derivatives toward the chemical plating on plastics." Biomacromolecules, Sep. 2002, vol. 3, No. 5, pp. 1120-1125.
Othman et al., "A comprehensive study of the spontaneous formation of nanoassemblies in water by a "lock-and-key" interaction between two associative polymers." Journal of Colloids and Interface Science, Feb. 2011, vol. 354, No. 2, pp. 517-527.
Sihorkar V. et al. "Potential of polysaccharide anchored liposomes in drug delivery, targeting and immunization." Journal of Pharmacy and Pharmaceutical Sciences, 2001, vol. 4, No. 2, pp. 138-158.
Mourya et al. "Chitosan-modifications and applications: opportunities galore." Reactive & Functional Polymers, vol. 68, 2006, pp. 1013-1051.
Duclairoir, C. et al. "Alpha-tocopherol encapsulation and in vitro release from wheat gliadin nanoparticles." Journal of Microencapsulation, Jan. 2002, vol. 19, No. 1, pp. 53-60.
Ezpeleta, I. et al. "Gliadin nanoparticles for the controlled release of all-trans-retinoic acid." Int. J. Pharm., 1996, vol. 131, pp. 191-200.
Veis, A. "The Macromolecular Chemistry of Gelatin." Academic Press. A.G.,1964.
Scheffel, U. et al. "Albumin microspheres for study of the reticuloendothelial system." J. Nucl. Med., Jul. 1972, vol. 13, No. 7, pp. 498-503.
Fujimoto, M. et al. "Effect of heating process on the formation of nanoparticles of elastin model polypeptide, (GVGVP) 251, by gamma-ray crosslinking." Polymer Bulletin, 2010, vol. 64, pp. 707-716.
Horsky, J. and Pitha, J. "Inclusion Complexes of Proteins: Interaction of cyclodextrins with peptides containing aromatic amino acids studied by competitive spectrophotometry." Journal of Inclusion Phenomena and Molecular Recognition in Chemistry, vol. 18, No. 3, Sep. 1994, pp. 291-300.
Itamar Shalit et al., "In Vitro Synergy of Caspofungin and Itraconazole against Aspergillus spp.: MIC versus Minimal Effective Concentration End Points", Antimicrobial Agents and Chemotherapy, vol. 47, No. 4, Apr. 2003, pp. 1416-1418.

* cited by examiner

ANTIPARASITIC AND/OR ANTIFUNGAL COMPOSITION COMPRISING HYDROPHOBISED CHITOSAN

FIELD OF THE INVENTION

The field of the invention is that of hydrophobised chitosan having biological activities, in particular antiparasitic and/or antifungal activities. As such, the present invention relates to a composition comprising hydrophobised chitosan and which can be used as an antiparasitic and/or antifungal agent or in the treatment of parasitic and/or fungal infections.

According to a first aspect, the field of the invention is that of antiparasitic agents. The present invention relates to a composition comprising hydrophobised chitosan having antiparasitic properties, with the hydrophobised chitosan having more preferably the form of nanoparticles. The composition of the invention can be used as an antiparasitic agent or in the treatment of parasitic infections.

According to a second aspect, the field of the invention is that of antifungal agents. The present invention relates to a composition comprising an antifungal agent and hydrophobised chitosan. The composition of the invention can be used as an antifungal agent or in the treatment of fungal infections. The association of the antifungal agent and hydrophobised chitosan makes it possible to increase the efficacy of the antifungal agent and to decrease the doses administered.

STATE OF THE ART

Parasitic and/or fungal infections are widespread and can have serious consequences, in particular in immunodepressed individuals.

Parasitic infections are caused by metazoans or protozoa that parasite the organism, such as for example *Leishmania, Trichomonas* or *Trypanosomes*.

*Trichomonas vaginalis* is a prostate parasite responsible for urogenital *trichomonas*, one of the most widespread sexually transmitted diseases. About 180 million people are infected in the world by this parasite; this disease has substantial consequences from a medical as well as social and economic standpoint.

The conventional treatment for urogenital *trichomonas* consists in the use of metronidazole (MTZ), a 5-nitroimidazole derivative of azomycin, the treatment is administered by oral route. However, the systemic absorption of such a molecule has a risk of allergy and favours the appearance of the phenomenon of resistance to this molecule. One of the disadvantages of MTZ is also its contraindication in pregnant women in the first months of pregnancy, in particular because of its possible mutagenic effect. No alternative treatment is available today and new approaches for the treatment of *trichomonas* are necessary.

The present invention therefore proposes a new antiparasitic therapeutic strategy based on the use of a composition comprising hydrophobised chitosan.

The hydrophobised chitosan of the invention can also be used in the treatment of fungal infections.

Invasive fungal infections are caused by fungal organisms of the yeast or filament type. The mushrooms responsible are most of the time inoffensive. However, when they infect an immunocompromised person afflicted, for example, with cancer, HIV (human immunodeficiency virus), or treated with immunosuppressants, these same mushrooms can be highly pathogenic. The mushrooms, responsible for infections in man, that are the most often isolated are *Candida* sp. and *Aspergillus* sp. Various treatments exist for treating fungal infections but the increase in their frequency for thirty years now, as well as the appearance of resistances, now make it necessary to develop new treatments.

Molecules with increasingly better performance such as third-generation azoles, polyenes or echinocandins, are today used to treat fungal infections. Azoles, such as itraconazole, voriconazole or fluconazole, are broad-spectrum antifungals which are effective but responsible for an increased risk of drug interactions and which result in hepatic disorders. Polyenes are voluminous amphiphilic molecules, such as nystatin or amphotericin B, also having a broad range of activity. However, nystatin is reserved for topical use because of high toxicity. Amphotericin B can however be administered by oral route but has a renal toxicity. Echinocandins aim to destroy the fungal cell wall by inhibiting the β (1-3)-D-glucan synthetase. These antifungals have a broad action spectrum and substantial efficacy but their use is at a very high cost and they are responsible for the appearance of resistant strains.

The current antifungals therefore have various disadvantages, linked primarily to the need to use substantial and/or repeated doses:
  existence of side effects;
  appearance of resistances, which can in particular have dramatic consequences in immunodepressed individuals;
  high cost of the treatments.

There is therefore a need for new antifungal treatments that make it possible to reduce the doses administered so as to limit the side effects, prevent the appearance of resistances and to decrease the cost of treatments.

Formulations have been proposed in order to vectorise antifungal agents and favour their availability. Vectorisation in particular makes it possible to convey the antifungal agent in the organism without it being altered or provoking side effects, then to release it on target tissue. By increasing the availability of the antifungal agent, less substantial doses can be administered for the same efficacy.

As such, amphotericin B (AmB) encapsulated in liposomes (Ambisome) is commercially available today. Amphotericin B also exists in the form of Abelcet, a formulation as a lipid bilayer. Work has moreover described the preparation of cationic lipid nanoparticles as vectors of amphotericin B (Vieira et al. *J. Nanobiotech.* 2008, 6:6). These nanoparticles were tested against the mushroom *C. albicans*: they showed an antifungal activity equivalent to that of Fungizone® (AmB in deoxycholate) while still limiting the nephrotoxicity.

Various formulations comprising chitosan have also been proposed. Chitosan is a natural polysaccharide which has the advantage of being biocompatible, biodegradable and bioadhesive. As such, liposomes of AmB coated with chitosan have been described in order to improve the pulmonary availability of AmB (Albasarah et al., *J. Pharmacy Pharmacol.*, 2010, 62, 821-828). Particles of chitosan have however been used to encapsulate AmB and have shown an antifungal efficacy equivalent to that of Fungizone®, while still having a reduced renal toxicity (Limpeanchob et al., *Naresuan Univ. J.*, 2006, 14(2) 27-34).

The formulations hereinabove therefore make it possible to decrease the side effects of amphotericin B and/or to improve bioavailability.

Another strategy to decrease the doses of antifungal administered is to provide antifungal agents that have more substantial biological activity. An increased efficacy can then be obtained for reduced doses.

As such, Gharib et al. have shown that nanospheres of PLGA (poly[lactid-co-glycolid]) loaded with AmB made it possible to reduce the toxicity of AmB and to increase its activity (Gharib et al. *DARU,* 2011, 19(5), 351-355). However, preparing nanospheres makes use of the technique of nanoprecipitation. This technique has the disadvantage of using toxic solvents such as acetone.

The present invention relates to a composition comprising an antifungal agent and modified chitosan (hydrophobised chitosan), with the modified chitosan able to form particles. As far as the Applicant is aware, particles constituted of hydrophobised chitosan of the invention have never been described in prior art. The preparation of the compositions of the invention is carried out via a simple mixing of the constituents. The Applicant has shown that composition of the invention has an antifungal activity that is higher than that of the antifungal agent alone and therefore makes it possible to decrease the doses required to treat fungal infections.

Definitions

In this invention, the terms herein below are defined in the following way:
"antifungal agent" refers to a substance that has the capacity to kill or limit the proliferation of microscopic mushrooms and of yeasts.
"antiparasitic agent" refers to a substance that has the capacity to kill or to limit the proliferation of parasites.
"chitosan" refers to a linear heteropolymer of D-glucosamine and of N-acetyl-D-glucosamine linked to b (1-4) according to the following formula:

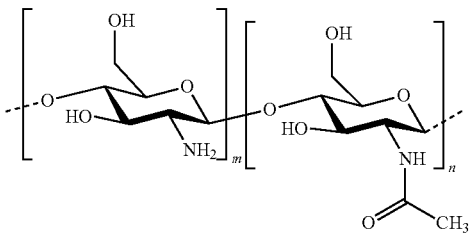

wherein m represents the number of D-glucosamine units and n represents the number of N-acetyl-D-glucosamine units; with the reserve that the percentage of m in relation to the total number of units is greater than 50%.
"hydrophobised chitosan" means that the chitosan has been made hydrophobic by grafting onto the hydroxyl and/or amine functions, chains that, by nature, are hydrophobic due to their apolar nature; preferably, alkyl or alkenyl chains. According to one preferred embodiment, the hydrophobised chitosan of the invention is amphiphilic.
"cyclodextrin" refers to a cyclic oligosaccharide of β-D-glucopyranose units connected by bonds α(1-4). Cyclodextrins are cage molecules. They exist in different sizes, all having the shape of a lampshade and carrying localised hydrophobic groups on the outside, with the cavity being relatively hydrophobic.
According to one preferred embodiment, the cyclodextrin used in the invention is "an α-cyclodextrin". This expression refers to α-cyclodextrin or a derivative of α-cyclodextrin, with the α-cyclodextrin being formed of 6 glucopyranose subunits. α-cyclodextrin is commercially available and is recognised as being a pharmaceutically accepted excipient by most pharmacopoeias.
"inclusion complex" designates a system that results from the interaction between a "host" molecule which admits inside its cavity one or several other "guest" molecules, without the establishing of any covalent bond. The expression "non-covalent inclusion complex" means that the constituents of the inclusion complex interact by Van-der-Waals bonds and/or hydrogen bonds, and/or electrostatic bonds, and/or hydrophobic bonds, excluding covalent bonds.
"hydrophobic group" refers to an apolar substitute, which cannot engage hydrogen bonds and which dissolves more easily in oil or other hydrophobic solvents than in water.
"alkyl" refers to a saturated, linear or branched hydrocarbon chain, comprising preferably from 1 to 20 carbon atoms; more preferably, methyl, ethyl, propyl, isopropyl, n-butyl, sec-butyl, isobutyl, tert-butyl, lauryl —C, or alkyl chains comprising 11, 13, 15 or 17 carbon atoms.
"alkenyl" refers to any linear or branched hydrocarbon chain, carrying at least one double bond; preferably 1, 2, 3 or 4 double bonds, of 2 to 20 carbon atoms. In one preferred embodiment of the invention, "alkenyl" refers to a linear hydrocarbon chain, carrying 1, 2 or 3 double bonds, and comprising 11, 13, 15 or 17 carbon atoms.
"poly(alkylcyanoacrylate)" refers to a polymer obtained by polymerisation of alkylcyanoacrylate units.
"pharmaceutically acceptable" refers to a compound that does not produce an allergic reaction or adverse reaction when it is administered to an animal, more preferably a human. The pharmaceutically acceptable excipients include all of the solvents, dispersion mediums, coatings, antibacterial and antifungal agents, isotonic agents, absorption delaying agents and other similar agents.
"patient" refers to a warm-blooded animal, more preferably a human being, which is waiting for the reception of, or is receiving medical care or is/will be the object of a medical procedure or is monitored for the development of a disease.

DETAILED DESCRIPTION

Composition

This invention relates to a composition comprising hydrophobised chitosan.

In one embodiment of the invention, the composition comprises:
hydrophobised chitosan with the general formula (I):

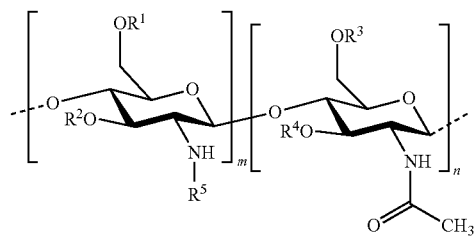

wherein
R¹, R², R³, R⁴ and R⁵ are identical or different, and represent:
a hydrogen atom;
a hydrophobic group;
a group substituted by a thiol function;
provided that at least one of R¹, R², R³, R⁴ and R⁵ is a hydrophobic group;
n and m each independently represent an integer between 1 and 3000, preferably between 5 and 1500, more preferably between 25 and 100, with the reserve that the percentage of m with respect to m+n is greater than 50%.

Hydrophobised Chitosan

According to an embodiment, the hydrophobised chitosan is composed of at least three saccharide units, preferably from 5 to 1500 saccharide units, more preferably from 25 to 100 saccharide units. In one embodiment, the hydrophobised chitosan with the formula (I) is such that m+n is at least equal to 3, preferably m+n ranges from 3 to 6000, more preferably from 5 to 1500. Since this entails chitosan, the percentage of m with respect to m+n (degree of acetylation) must be greater than 50%. A degree of acetylation less than 50% corresponds to chitin.

According to one embodiment, the molar weight of the hydrophobised chitosan is between 5 kDa and 100,000 kDa; preferably, between 50 kDa and 10,000 kDa; more preferably between 100 kDa and 1000 kDa. According to one preferred embodiment, the molar weight of the hydrophobised chitosan is equal to 10 kDa, 20 kDa, 145 kDa or 250 kDa.

According to one embodiment of this invention, hydrophobised chitosan has a degree of substitution by the hydrophobic groups ranging from 0.001 to 100%; e preferably from 0.05 to 70%, more preferably, from 0.1 to 50%, more preferably, from 1 to 20%. The degree of substitution reflects the number of hydrophobic groups linked to 100 saccharide units of the polysaccharide chain of the chitosan. It can be determined by the experimental conditions of the grafting and can be measured by NMR or by elementary analysis for example.

According to one embodiment, the hydrophobic groups are bonded covalently to the chitosan by one or several nitrogen atoms of said chitosan. According to another embodiment, the hydrophobic groups are bonded covalently to the chitosan by one or several oxygen atoms of said chitosan. In another embodiment the hydrophobic groups are bonded covalently to the chitosan by one or several nitrogen atoms and/or one or several oxygen atoms of said chitosan.

According to one embodiment, the hydrophobised chitosan used in the composition of the invention is obtained by synthesis methods known to those skilled in the art. In particular, the functionalisation of the chitosan over one or several of its nitrogen atoms by hydrophobic chains can be carried out by N-acylation, in the presence of a coupling agent and of a fatty acid. The functionalisation of the chitosan over one or several of its oxygen atoms by hydrophobic chains can be carried out by O-acylation, in the presence of a fatty acid. Synthesis methods of the hydrophobised chitosan according to the invention are presented in the experimental part.

According to one embodiment, the hydrophobised chitosan with the general formula (I) is such that the hydrophobic group is selected from:

a group with the formula —COR⁶, wherein R⁶ represents:
a linear or branched alkyl group, comprising from 1 to 1000 carbon atoms, preferably from 1 to 20 carbon atoms, more preferably the groups —(CH₂)₁₄—CH₃ or —(CH₂)₁₆—CH₃;
a linear or branched alkenyl group, comprising from 2 to 1000 carbon atoms; preferably from 2 to 20 carbon atoms, and comprising at least one double bond C=C; more preferably, from 1 to 4 double bonds, more preferably the groups —(CH₂)₇—CH=CH—CH₂—(CH₂)₇—CH₃ or —(CH₂)₇—CH=CH—(CH₂)₇—CH₃;
a poly(alkylcyanoacrylate) wherein the alkyl is linear or branched, comprising from 1 to 12 carbon atoms; preferably, the alkyl is a methyl, propyl, isopropyl, butyl, isobutyl, pentyl, isopentyl, hexyl, isohexyl, heptyl, isoheptyl, octyl, isooctyl, nonyl, isononyl, decyl, isodecyl, undecyl, iso-undecyl, dodecyl, isododecyl and derivatives, more preferably, the poly(alkylcyanoacrylate) is poly(isobutylcyanoacrylate).

According to one embodiment, the hydrophobised chitosan with the general formula (I) is such that the group substituted by a thiol function is an alkyl substituted by a thiol function, an alkenyl substituted by a thiol function or a group —C(=NH₂⁺X⁻)—(CH₂)_q—SH wherein X represents a halogen; preferably Cl, and q represents an integer ranging from 1 to 10; preferably, 1, 2, 3, 4, or 5.

According to one embodiment, the hydrophobised chitosan is with the general formula (I):

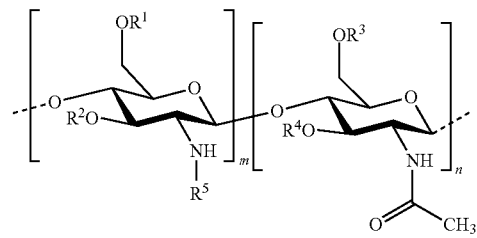

wherein
R¹, R², R³, R⁴ and R⁵ are identical or different, and represent:
a hydrogen atom;
a hydrophobic group selected from:
a group with the formula —COR⁶, wherein R⁶ represents:
a linear or branched alkyl group, comprising from 1 to 1000 carbon atoms; preferably, from 1 to 20 carbon atoms; more preferably, the groups —(CH₂)₁₄—CH₃ or —(CH₂)₁₆—CH₃;
a linear or branched alkenyl group, comprising from 2 to 1000 carbon atoms; preferably, from 2 to 20 carbon atoms, and comprising at least one double bond C=C; more preferably, from 1 to 4 double bonds; more preferably, the groups —(CH₂)₇—CH=CH—CH₂—(CH₂)₇—CH₃ or —(CH₂)₇—CH=CH—(CH₂)₇—CH₃;
a poly(alkylcyanoacrylate) wherein the alkyl is linear or branched, comprising from 1 to 12 carbon atoms; preferably, the alkyl is a methyl, propyl, isopropyl, butyl, isobutyl, pentyl, isopentyl, hexyl, isohexyl, heptyl, isoheptyl, octyl, isooctyl, nonyl, isononyl, decyl, isodecyl, undecyl, iso-undecyl, dodecyl, isododecyl and derivatives; more p preferably, the poly(alkyl-cyanoacrylate) is poly(isobutylcyanoacrylate);
a group substituted by a thiol function; preferably, an alkyl substituted by a thiol function, an alkenyl substituted by a thiol function or a group —C(=NH$_2$$^+$X$^-$)—(CH$_2$)$_q$—SH wherein X represents a halogen; preferably Cl, and q represents an integer ranging from 1 to 10; preferably 1, 2, 4, or 5;
provided that at least one of R$^1$, R$^2$, R$^3$, R$^4$ and R$^5$ is a hydrophobic group;
n and m each independently represent an integer between 1 and 3000, preferably, between 5 and 1500; more preferably, between 25 and 100, provided that the percentage of m with respect to m+n is greater than 50%.

According to one embodiment, the hydrophobised chitosan is with the general formula (Ia):

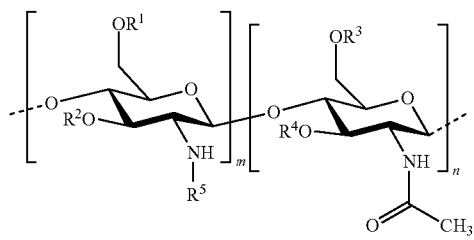

wherein
R$^1$, R$^2$, R$^3$, R$^4$ and R$^5$ are identical or different, and represent:
a hydrogen atom;
a hydrophobic group with the formula —COR$^6$, wherein R$^6$ represents:
a linear or branched alkyl group, comprising from 1 to 1000 carbon atoms; preferably, from 1 to 20 carbon atoms; more preferably, the groups —(CH$_2$)$_{14}$—CH$_3$ or —(CH$_2$)$_{16}$—CH$_3$;
a linear or branched alkenyl group, comprising from 2 to 1000 carbon atoms; preferably, from 2 to 20 carbon atoms, and comprising at least one double bond C=C; more preferably, from 1 to 4 double bonds, more preferably, the groups —(CH$_2$)$_7$—CH=CH—CH$_2$—(CH$_2$)$_7$—CH$_3$ or —(CH$_2$)$_7$—CH=CH—(CH$_2$)$_7$—CH$_3$;
a group substituted by a thiol function; preferably, an alkyl substituted by a thiol function, an alkenyl substituted by a thiol function or a group —C(=NH$_2$$^+$X$^-$)—(CH$_2$)$_q$—SH wherein X represents a halogen; preferably, Cl, and q represents an integer ranging from 1 to 10; preferably 1, 2, 4, or 5;
provided that at least one of R$^1$, R$^2$, R$^3$, R$^4$ and R$^5$ is a hydrophobic group;
n and m each independently represent an integer between 1 and 3000, preferably between 5 and 1500, more preferably between 25 and 100, provided that the percentage of m with respect to m+n is greater than 50%.

According to one preferred embodiment, the hydrophobic groups carried by the hydrophobised chitosan with the formula (Ia) are obtained by coupling on the amine and/or hydroxyl functions of the chitosan lauric acid, palmitic acid, oleic acid, stearic acid, linoleic acid, with this list not being limiting in any case.

According to one embodiment, the hydrophobised chitosan is with the general formula (Ib):

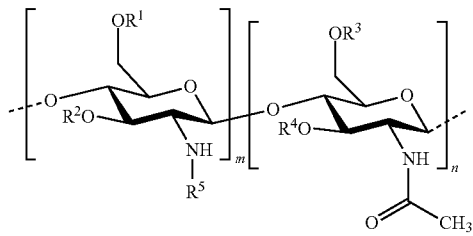

wherein
R$^1$, R$^2$, R$^3$, R$^4$ and R$^5$ are identical or different, and represent:
a hydrogen atom;
a poly(alkylcyanoacrylate) hydrophobic group wherein the alkyl is linear or branched, comprising from 1 to 12 carbon atoms, preferably the alkyl is a methyl, propyl, isopropyl, butyl, isobutyl, pentyl, isopentyl, hexyl, isohexyl, heptyl, isoheptyl, octyl, isooctyl, nonyl, isononyl, decyl, isodecyl, undecyl, iso-undecyl, dodecyl, isododecyl and derivatives, more preferably the poly(alkylcyanoacrylate) is poly(isobutylcyanoacrylate);
a group substituted by a thiol function, preferably an alkyl substituted by a thiol function, an alkenyl substituted by a thiol function or a group —C(=NH$_2$$^+$X$^-$)—(CH$_2$)$_q$—SH wherein X represents a halogen, preferably Cl, and q represents an integer ranging from 1 to 10, preferably 1, 2, 4, or 5;
provided that at least one of R$^1$, R$^2$, R$^3$, R$^4$ and R$^5$ is a hydrophobic group;
n and m each independently represent an integer between 1 and 3000, preferably between 5 and 1500, more preferably between 25 and 100, provided that the percentage of m with respect to m+n is greater than 50%.

According to one particular embodiment, the hydrophobised chitosan is with the general formula (Ib) wherein R$^5$ represents a poly(alkylcyanoacrylate) hydrophobic group wherein the alkyl is linear or branched, comprising from 1 to 12 carbon atoms, preferably the alkyl is a methyl, propyl, isopropyl, butyl, isobutyl, pentyl, isopentyl, hexyl, isohexyl, heptyl, isoheptyl, octyl, isooctyl, nonyl, isononyl, decyl, isodecyl, undecyl, iso-undecyl, dodecyl, isododecyl and derivatives, more preferably the poly(alkylcyanoacrylate) is poly(isobutylcyanoacrylate).

According to one particular embodiment, the hydrophobised chitosan is with the general formula (Ib) wherein R$^5$ represents a poly(alkylcyanoacrylate) hydrophobic group such as defined hereinabove and at least one of R$^1$, R$^2$, R$^3$ and R$^4$ represent a group substituted by a thiol function.

According to another particular embodiment, the hydrophobised chitosan is with the general formula (Ib) wherein R$^5$ represents a poly(alkylcyanoacrylate) hydrophobic group such as defined hereinabove and R$^1$, R$^2$, R$^3$ and R$^4$ represent H.

According to one preferred embodiment, the composition of the invention comprises hydrophobised chitosan with the general formula (Ib) such as described hereinabove.

According to one embodiment, the hydrophobised chitosan with the general formula (Ib) is present in the form of particles in the composition of the invention, preferably in the form of nanoparticles or of microparticles.

According to one embodiment, the size of the nanoparticles of hydrophobised chitosan with the general formula (Ib) is between 10 and 200000 nm, preferably between 50 and 100,000 nm, more preferably between 100 and 80000 nm.

According to one embodiment, the particles of hydrophobised chitosan with the general formula (Ib) comprising poly(alkylcyanoacrylate) chains are obtained by anionic or radical polymerisation, more preferably in emulsion, using chitosan and alkylcyanoacrylate monomer.

According to one preferred embodiment, the composition of the invention comprises:
(i) hydrophobised chitosan with the general formula (Ib) wherein $R^5$ represents a poly(alkylcyanoacrylate) hydrophobic group such as defined hereinabove and at least one of $R^1$, $R^2$, $R^3$ and $R^4$ represent a group substituted by a thiol function; and
(ii) hydrophobised chitosan with the general formula (Ib) wherein $R^5$ represents a poly(alkylcyanoacrylate) hydrophobic group such as defined hereinabove and $R^1$, $R^2$, $R^3$ and $R^4$ represent H.

According to one particular embodiment, the composition of the invention comprises from 0% to 100% by weight of hydrophobised chitosan (i) with respect to the total weight of hydrophobised chitosan present in the composition, preferably from 25 to 75%.

According to one particular embodiment, the composition of the invention comprises 25% by weight of hydrophobised chitosan (i) and 75% by weight of hydrophobised chitosan (ii), with respect to the total weight of hydrophobised chitosan present in the composition.

According to one particular embodiment, the composition of the invention comprises 50% by weight of hydrophobised chitosan (i) and 50% by weight of hydrophobised chitosan (ii), with respect to the total weight of hydrophobised chitosan present in the composition.

According to one particular embodiment, the composition of the invention comprises 75% by weight of hydrophobised chitosan (i) and 25% by weight of hydrophobised chitosan (ii), with respect to the total weight of hydrophobised chitosan present in the composition.

Hydrophobised Chitosan+Cyclodextrin

The composition of the invention can furthermore comprise an α-cyclodextrin.

In an embodiment, the hydrophobised chitosan forms with the α-cyclodextrin a non-covalent inclusion complex. The non-covalent inclusion complex can form particles.

According to one embodiment, the composition of the invention comprises an α-cyclodextrin present in the form of a monomer and forming with the hydrophobised chitosan with the general formula (I) a non-covalent inclusion complex.

According to one embodiment, an α-cyclodextrin is present in the composition of the invention. The α-cyclodextrin can be substituted or unsubstituted. "Substituted cyclodextrin" means for example a cyclodextrin substituted by an alkyl group, by a hydroxyalkyl group, by a maltosyl group or by a galactosyl group.

According to one embodiment, an α-cyclodextrin is present in the composition of the invention and is with the general formula (II):

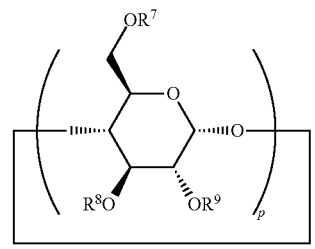

wherein
p is equal to 6,
$R^7$, $R^8$ and $R^9$ are identical or different, preferably identical, and each independently represent a hydrogen atom; an alkyl group comprising 1 to 4 carbon atoms, preferably selected from the group comprising methyl, ethyl, propyl, and isopropyl; $-NH_2$, $-NH_3^+$, or $-SO_4^{2-}$; preferably, $R^7$, $R^8$ and $R^9$ each independently represent a hydrogen atom or a methyl group.

According to one preferred embodiment, an α-cyclodextrin is present in the composition of the invention and is present in the form of an α-cyclodextrin functionalisation by a ligand chosen from antibodies, fragments of antibodies, acceptors, lectins, biotin or derivatives thereof.

In one embodiment of the invention, the composition comprises:
hydrophobised chitosan with the general formula (I):

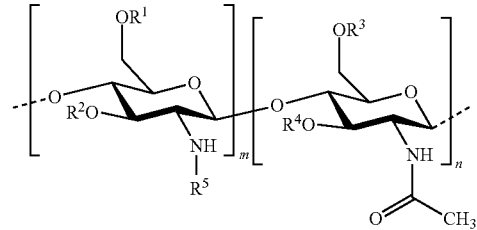

wherein
$R^1$, $R^2$, $R^3$, $R^4$ and $R^5$ are identical or different, and represent:
a hydrogen atom;
a hydrophobic group selected from:
a group with the formula $-COR^E$, wherein $R^6$ represents:
a linear or branched alkyl group, comprising from 1 to 1000 carbon atoms, preferably from 1 to 20 carbon atoms, more preferably the groups $-(CH_2)_{14}-CH_3$ or $-(CH_2)_{16}-CH_3$;
a linear or branched alkenyl group, comprising from 2 to 1000 carbon atoms, preferably from 2 to 20 carbon atoms, and comprising at least one double bond C=C, more preferably from 1 to 4 double bonds, more preferably the groups $-(CH_2)_7-CH=CH-CH_2-(CH_2)_7-CH_3$ or $-(CH_2)_7-CH=CH-(CH_2)_7-CH_3$;
a poly(alkylcyanoacrylate) wherein the alkyl is linear or branched, comprising from 1 to 12 carbon atoms, preferably the alkyl is a methyl, propyl, isopropyl, butyl, isobutyl, pentyl, isopentyl, hexyl, isohexyl, heptyl, isoheptyl, octyl, isooctyl, nonyl, isononyl, decyl, isodecyl, undecyl, iso-undecyl, dodecyl, isododecyl and derivatives, more preferably the poly(alkylcyanoacrylate) is poly(isobutylcyanoacrylate);

a group substituted by a thiol function, preferably an alkyl substituted by a thiol function, an alkenyl substituted by a thiol function or a group —C(=NH$_2^+$X$^-$)—(CH$_2$)$_q$—SH wherein X represents a halogen, preferably Cl, and q represents an integer ranging from 1 to 10, preferably 1, 2, 3, 4, or 5;

provided that at least one of R$^1$, R$^2$, R$^3$, R$^4$ and R$^5$ is a hydrophobic group;

n and m each independently represent an integer between 1 and 3000, preferably between 5 and 1500, more preferably between 25 and 100, provided that the percentage of m with respect to m+n is greater than 50%;

optionally an α-cyclodextrin, said α-cyclodextrin being in the form of a monomer, and when it is present, the α-cyclodextrin forms with the hydrophobised chitosan with the general formula (I) a non-covalent inclusion complex.

According to one aspect of the invention, the composition of the invention comprises:

hydrophobised chitosan with the general formula (Ia) such as described hereinabove;

an α-cyclodextrin, said α-cyclodextrin being in the form of a monomer, and forming with the hydrophobised chitosan with the general formula (Ia) a non-covalent inclusion complex.

In this aspect of the invention, according to one preferred embodiment, the α-cyclodextrin is with the general formula (II), such as described hereinabove.

According to one embodiment, the hydrophobised chitosan with the general formula (Ia) forms with the α-cyclodextrin a non-covalent inclusion complex. The inclusion complexes form particles, preferably nanoparticles or microparticles.

In one embodiment, the size of the inclusion complex particles is between 10 and 200000 nm, preferably between 50 and 100000 nm. According to one embodiment, the inclusion complex particles are nanoparticles of which the size is between 10 and 1000 nm, preferably between 50 and 1000 nm. According to one embodiment, the inclusion complex particles are microparticles of which the size is between 1000 and 50000 nm, preferably between 1000 and 10000 nm.

Advantageously, the ratio between the concentration of α-cyclodextrin and the concentration of the hydrophobised chitosan with the general formula (Ia) at a value ranging from 0.01 to 1500, preferably from 4 to 15, more preferably equal to 10. By modifying this concentration ratio, it is possible to modulate the size of the particles obtained using inclusion complexes.

According to one embodiment, in the inclusion complex particle of hydrophobised chitosan with the general formula (Ia) and of α-cyclodextrin, preferably α-cyclodextrin with the formula (II), the hydrophobised chitosan with the general formula (Ia) is present at a concentration ranging from 0.1 to 30% by weight with respect to the total weight of the particle, preferably from 0.5 to 20%, more preferably from 0.5 to 10%.

According to one embodiment, in the inclusion complex particle of hydrophobised chitosan with the general formula (Ia) and of α-cyclodextrin, preferably α-cyclodextrin with the formula (II), the α-cyclodextrin is present at a concentration ranging from 0.1 to 99% by weight with respect to the total weight of the particle, preferably from 4 to 25%, more preferably equal to 10%.

Hydrophobised Chitosan+Antifungal Agent

The composition of the invention can furthermore comprise an active agent, such as for example an antifungal agent.

This invention therefore also relates to a composition comprising an active agent and hydrophobised chitosan. In particular, this invention relates to a composition comprising an antifungal agent and hydrophobised chitosan.

In one embodiment, the hydrophobised chitosan is present in the composition of the invention in the form of particles. In one first embodiment, the antifungal agent and the particles of hydrophobised chitosan are combined together in the composition of the invention, i.e. the antifungal agent is not encapsulated, it is simply mixed with the hydrophobised chitosan particles. In one second embodiment, the antifungal agent is encapsulated by the particles of hydrophobised chitosan, i.e. a portion of the antifungal agent is "trapped" inside the particle and a portion is outside the particle.

According to one embodiment, the composition of the invention further comprises an α-cyclodextrin. In one embodiment, the hydrophobised chitosan forms with the α-cyclodextrin a non-covalent inclusion complex. The non-covalent inclusion complex can form particles. In one first embodiment, the antifungal agent and the inclusion complex of hydrophobised chitosan and of cyclodextrin are combined together in the composition of the invention. In a second embodiment, the antifungal agent is encapsulated by the inclusion complex of hydrophobised chitosan and of cyclodextrin.

In one embodiment of the invention, the composition comprises:

at least one antifungal agent;

hydrophobised chitosan with the general formula (I):

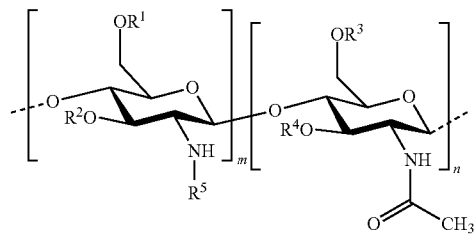

wherein

R$^1$, R$^2$, R$^3$, R$^4$ and R$^5$ are identical or different, and represent:

a hydrogen atom;

a hydrophobic group;

a group substituted by a thiol function;

provided that at least one of R$^1$, R$^2$, R$^3$, R$^4$ and R$^5$ is a hydrophobic group;

n and m each independently represent an integer between 1 and 3000, preferably between 5 and 1500, more preferably between 25 and 100, provided that the percentage of m with respect to m+n is greater than 50%.

According to one embodiment, the hydrophobised chitosan with the general formula (I) is such that the hydrophobic group is selected from:

a group with the formula —COR$^6$, wherein R$^6$ represents:
  a linear or branched alkyl group, comprising from 1 to 1000 carbon atoms, preferably from 1 to 20 carbon atoms, more preferably the groups —(CH$_2$)$_{14}$—CH$_3$ or —(CH$_2$)$_{16}$—CH$_3$;
  a linear or branched alkenyl group, comprising from 2 to 1000 carbon atoms, preferably from 2 to 20 carbon atoms, and comprising at least one double bond C=C, preferably from 1 to 4 double bonds, preferably the groups —(CH$_2$)$_7$—CH=CH—CH$_2$—(CH$_2$)$_7$—CH$_3$ or —(CH$_2$)$_7$—CH=CH—(CH$_2$)$_7$—CH$_3$;
a poly(alkylcyanoacrylate) wherein the alkyl is linear or branched, comprising from 1 to 12 carbon atoms, preferably the alkyl is a methyl, propyl, isopropyl, butyl, isobutyl, pentyl, isopentyl, hexyl, isohexyl, heptyl, isoheptyl, octyl, isooctyl, nonyl, isononyl, decyl, isodecyl, undecyl, iso-undecyl, dodecyl, isododecyl and derivatives, more preferably the poly(alkylcyanoacrylate) is poly(isobutylcyanoacrylate).

According to one embodiment, the hydrophobised chitosan with the general formula (I) is such that the group substituted by a thiol function is an alkyl substituted by a thiol function, an alkenyl substituted by a thiol function or a group —C(=NH$_2^+$X$^-$)—(CH$_2$)$_q$—SH wherein X represents a halogen, preferably Cl, and q represents an integer ranging from 1 to 10, preferably 1, 2, 3, 4, or 5.

According to one embodiment, the composition of the invention further comprises an α-cyclodextrin, said α-cyclodextrin being in the form of a monomer and forming with the hydrophobised chitosan with the general formula (I) a non-covalent inclusion complex.

In one embodiment of the invention, the composition comprises:
  at least one antifungal agent;
  hydrophobised chitosan with the general formula (I):

$$\left[\begin{array}{c}\text{OR}^1\\ \text{R}^2\text{O}\\ \text{NH}\\ \text{R}^5\end{array}\right]_m \left[\begin{array}{c}\text{OR}^3\\ \text{R}^4\text{O}\\ \text{NH}\\ \text{O}=\text{CH}_3\end{array}\right]_n$$

wherein
  R$^1$, R$^2$, R$^3$, R$^4$ and R$^5$ are identical or different, and represent:
    a hydrogen atom;
    a hydrophobic group selected from:
      a group with the formula —COR$^6$, wherein R$^6$ represents:
        a linear or branched alkyl group, comprising from 1 to 1000 carbon atoms, preferably from 1 to 20 carbon atoms, more preferably the groups —(CH$_2$)$_{14}$—CH$_3$ or —(CH$_2$)$_{16}$—CH$_3$;
        a linear or branched alkenyl group, comprising from 2 to 1000 carbon atoms, preferably from 2 to 20 carbon atoms, and comprising at least one double bond C=C, preferably from 1 to 4 double bonds, more preferably the groups —(CH$_2$)$_7$—CH=CH—CH$_2$—(CH$_2$)$_7$—CH$_3$ or —(CH$_2$)$_7$—CH=CH—(CH$_2$)$_7$—CH$_3$;
      a poly(alkylcyanoacrylate) wherein the alkyl is linear or branched, comprising from 1 to 12 carbon atoms, preferably the alkyl is a methyl, propyl, isopropyl, butyl, isobutyl, pentyl, isopentyl, hexyl, isohexyl, heptyl, isoheptyl, octyl, isooctyl, nonyl, isononyl, decyl, isodecyl, undecyl, iso-undecyl, dodecyl, isododecyl and derivatives, more preferably the poly(alkylcyanoacrylate) is poly(isobutylcyanoacrylate);
      a group substituted by a thiol function, preferably an alkyl substituted by a thiol function, an alkenyl substituted by a thiol function or a group —C(=NH$_2^+$X$^-$)—(CH$_2$)$_q$—SH wherein X represents a halogen, preferably Cl, and q represents an integer ranging from 1 to 10, preferably 1, 2, 3, 4, or 5;
    provided that at least one of R$^1$, R$^2$, R$^3$, R$^4$ and R$^5$ is a hydrophobic group;
    n and m each independently represent an integer between 1 and 3000, preferably between 5 and 1500, more preferably between 25 and 100, provided that the percentage of m with respect to m+n is greater than 50%;
  optionally an α-cyclodextrin, said α-cyclodextrin being in the form of a monomer, and when it is present, the α-cyclodextrin forms with the hydrophobised chitosan with the general formula (I) a non-covalent inclusion complex.

According to one preferred embodiment, the composition of the invention comprises:
  at least one antifungal agent; and
  hydrophobised chitosan with the general formula (Ib) such as described hereinabove.

According to one embodiment, the hydrophobised chitosan with the general formula (Ib) is present in the form of particles in the composition of the invention, preferably in the form of nanoparticles or of microparticles.

According to one embodiment, the size of the nanoparticles of hydrophobised chitosan with the general formula (Ib) is between 10 and 200000 nm, preferably between 50 and 100,000 nm, more preferably between 100 and 80000 nm.

According to one embodiment, the particles of hydrophobised chitosan with the general formula (Ib) comprising poly(alkylcyanoacrylate) chains are obtained by anionic or radical polymerisation, preferably in emulsion, using chitosan and alkylcyanoacrylate monomer.

In one first embodiment of the invention, the antifungal agent and the particles of hydrophobised chitosan with the general formula (Ib) are combined together in the composition of the invention. In one second embodiment, the antifungal agent is encapsulated by the particles of hydrophobised chitosan with the general formula (Ib).

According to one embodiment, the composition of the invention comprises an antifungal agent selected from a group comprising:
  polyenes, such as for example amphotericin B, candicidin, filipin, hamycin, natamycin, nystatin, rimocidine;
  imidazole compounds such as for example bifonazole, butoconazole, clotrimazole, econazole, fenticonazole, isoconazole, ketoconazole, miconazole, omoconazole, oxiconazole, sertaconazole, sulconazole, tioconazole;
  triazole compounds, such as for example albaconazole, fluconazole, isavuconazole, itraconazole, posaconazole, ravuconazole, terconazole, voriconazole;
  thiazole compounds, such as for example abafungine;

allylamines, such as for example amorolfine, butenafine, naftifine, terbinafine;

echinocandins, such as for example anidulafungine, caspofungine, micafungine;

benzoic acid, cerulenine, ciclopirox, olamine, flucytosine, 5-fluorocytosine, griseofulvine, haloprogine, polygodial, tolnaftate, undecylenic acid, crystal violet; or chlorhexidine, polyvinylpyrrolidone (PVP) iodine (Betadine®), benzalkonium chloride (vaginal ovules or cream Pharmatex®), chlorine (Dakin).

According to one preferred embodiment, the antifungal agent is amphotericin B or chlorhexidine, preferably amphotericin B.

Hydrophobised Chitosan+Cyclodextrin+Antifungal Agent

According to one first aspect, the composition of the invention comprises:

at least one antifungal agent;

hydrophobised chitosan with the general formula (Ia) such as described hereinabove;

an α-cyclodextrin, said α-cyclodextrin being in the form of a monomer, and forming with the hydrophobised chitosan with the general formula (Ia) a non-covalent inclusion complex.

According to one preferred embodiment, the α-cyclodextrin is with the general formula (II), such as described hereinabove.

According to one embodiment, the hydrophobised chitosan with the general formula (Ia) forms with the α-cyclodextrin a non-covalent inclusion complex. The inclusion complexes form particles, preferably nanoparticles or microparticles.

In one embodiment, the size of the inclusion complex particles is between 10 and 200000 nm, preferably between 50 and 100000 nm. According to one embodiment, the inclusion complex particles are nanoparticles of which the size is between 10 and 1000 nm, preferably between 50 and 1000 nm. According to one embodiment, the inclusion complex particles are microparticles of which the size is between 1000 and 50000 nm, preferably between 1000 and 10000 nm.

Advantageously, the ratio between the concentration of α-cyclodextrin and the concentration of the hydrophobised chitosan at a value ranging from 0.01 to 1500, preferably from 4 to 15, more preferably equal to 10. By modifying this concentration ratio, it is possible to modulate the size of the particles obtained using inclusion complexes.

According to one embodiment, in the inclusion complex particle of hydrophobised chitosan with the general formula (Ia) and of α-cyclodextrin, preferably α-cyclodextrin with the formula (II), the hydrophobised chitosan with the general formula (Ia) is present at a concentration ranging from 0.1 to 30% by weight with respect to the total weight of the particle, preferably from 0.5 to 20%, more preferably from 0.5 to 10%.

According to one embodiment, in the inclusion complex particle of hydrophobised chitosan with the general formula (Ia) and of α-cyclodextrin, preferably α-cyclodextrin with the formula (II), the α-cyclodextrin is present at a concentration ranging from 0.1 to 99% by weight with respect to the total weight of the particle, preferably from 4 to 25%, more preferably equal to 10%.

In one first embodiment of the invention, the antifungal agent and the inclusion complex particles of hydrophobised chitosan with the formula (Ia) and of cyclodextrin are combined together in the composition of the invention. In one second embodiment, the antifungal agent is encapsulated by the inclusion complex particles of hydrophobised chitosan with the formula (Ia) and of cyclodextrin.

According to one second aspect, the composition of the invention comprises:

at least one antifungal agent;

hydrophobised chitosan with the general formula (Ib) such as described hereinabove;

optionally an α-cyclodextrin, said α-cyclodextrin being in the form of a monomer, and when it is present, the α-cyclodextrin forms with the hydrophobised chitosan with the general formula (Ib) a non-covalent inclusion complex.

According to one preferred embodiment, the composition of the invention comprises:

at least one antifungal agent; and hydrophobised chitosan with the general formula (Ib) such as described hereinabove.

According to one embodiment, the hydrophobised chitosan with the general formula (Ib) is present in the form of particles in the composition of the invention, preferably in the form of nanoparticles or of microparticles.

According to one embodiment, the size of the nanoparticles of hydrophobised chitosan with the general formula (Ib) is between 10 and 200000 nm, preferably between 50 and 100000 nm, more preferably between 100 and 80000 nm.

According to one embodiment, the particles of hydrophobised chitosan with the general formula (Ib) comprising poly(alkylcyanoacrylate) chains are obtained by anionic or radical polymerisation, preferably in emulsion, using chitosan and alkylcyanoacrylate monomer.

In one first embodiment of the invention, the antifungal agent and the particles of hydrophobised chitosan with the general formula (Ib) are combined together in the composition of the invention. In one second embodiment, the antifungal agent is encapsulated by the particles of hydrophobised chitosan with the general formula (Ib).

According to one embodiment, the hydrophobised chitosan with the general formula (Ib) forms with the α-cyclodextrin non-covalent inclusion complex. The inclusion complex forms a particle, preferably a nanoparticle or a microparticle.

In one first embodiment of the invention, the antifungal agent and the inclusion complex particles, formed from particles of hydrophobised chitosan with the general formula (Ib) and from cyclodextrin, are combined together in the composition of the invention. In one second embodiment, the antifungal agent is encapsulated by the inclusion complex particles of particles of hydrophobised chitosan with the general formula (Ib) and of cyclodextrin.

Method of Manufacturing the Composition of the Invention

The present invention also relates to a method of manufacturing the composition according to the invention.

According to a first aspect, the method of manufacturing of the composition according to the invention comprises a step for formation of particles of hydrophobised chitosan: hydrophobised chitosan with the general formula (I) such as described hereinabove is placed in a solvent, preferably water, optionally in the presence of an α-cyclodextrin, under stirring, in order to form a suspension of particles.

According to one particular embodiment, a mixture of different hydrophobised chitosans with the general formula (I) may be used to prepare the particles of hydrophobised chitosan of the composition of the invention.

Advantageously, the particles of hydrophobised chitosan formed by the method of the invention are nanoparticles or microparticles. When an α-cyclodextrin is present, there is preferentially a formation of non-covalent inclusion complexes between the hydrophobised chitosan and the α-cyclodextrin. The inclusion complexes can form particles, preferably nanoparticles or microparticles.

According to one particular embodiment of the invention, during the step of forming the particles, the hydrophobised chitosan is solubilised at a concentration ranging from 0.01 to 9000 g/L, preferably ranging from 1 to 600 g/L, and in particular about equal to 10 g/L, with the aqueous solvent chosen from pure water, an aqueous solution with a pH ranging from 1 to 7 or from 7 to 14, preferably from 5 to 7, or a solution of physiological serum optionally enriched with glucose or containing any other excipient for pharmaceutical, medical, paramedical, medical devices, animal feed, cosmetic, veterinary, agro-food, pesticides, cosmeto-textile, perfumery, environmental field or in the paint, packaging, building and/or automobile industry.

Alternatively, during the step of forming the particles, the hydrophobised chitosan is dispersed in an aqueous medium chosen from pure water, an aqueous solution with a pH ranging from 1 to 7 or from 7 to 14, preferably from 5 to 7, or a solution of physiological serum optionally enriched with glucose or containing any other excipient for pharmaceutical, medical, paramedical, medical devices, animal feed, cosmetic, veterinary, agro-food, pesticides, cosmeto-textile, perfumery, environmental field (depollution of water for example) or in the paint, packaging, building and/or automobile industry.

When the composition of the invention comprises an active agent, preferably an antifungal agent, the method of manufacturing of the composition according to the invention can be a method of association or a method of encapsulation.

According to a first aspect, the invention relates to a method of association, for the preparing of a composition according to the invention.

In one embodiment, the method of association for the preparing of a composition according to the invention, comprises the following steps:
(a) hydrophobised chitosan with the general formula (I) such as described hereinabove, is placed in a solvent, preferably water, optionally in the presence of an α-cyclodextrin, under stirring, in order to form a suspension of particles;
(b) at least one antifungal is added to the suspension.

Advantageously, during the step (a), when the hydrophobised chitosan is placed in the solvent, there is a formation of particles, preferably of nanoparticles or of microparticles. When an α-cyclodextrin is present, there is preferentially a formation of non-covalent inclusion complexes between the hydrophobised chitosan and the α-cyclodextrin. The inclusion complexes can form particles, preferably nanoparticles or microparticles.

According to one particular embodiment of the invention, during the step (a), the hydrophobised chitosan is:
in an aqueous solution at a concentration ranging from 0.01 to 9000 g/L, preferably ranging from 1 to 600 g/L, and in particular about equal to 10 g/L, with the aqueous solvent chosen from pure water, an aqueous solution with a pH ranging from 1 to 7 or from 7 to 14, preferably from 5 to 7, or a solution of physiological serum optionally enriched with glucose or containing any other excipient for pharmaceutical, medical, paramedical, medical devices, animal feed, cosmetic, veterinary, agro-food, pesticides, cosmeto-textile, perfumery, environmental field or in the paint, packaging, building and/or automobile industry;

or in dispersion in an aqueous medium chosen from pure water, an aqueous solution with a pH ranging from 1 to 7 or from 7 to 14, preferably from 5 to 7, or a solution of physiological serum optionally enriched with glucose or containing any other excipient for pharmaceutical, medical, paramedical, medical devices, animal feed, cosmetic, veterinary, agro-food, pesticides, cosmeto-textile, perfumery, environmental field (depollution of water for example) or in the paint, packaging, building and/or automobile industry.

According to a second aspect, the invention relates to a method of encapsulation, for preparing of a composition according to the invention.

In one embodiment, the method of encapsulation for preparing of a composition according to the invention, comprises the following steps:
(a) at least one antifungal agent is dissolved in a solvent, preferably water;
(b) hydrophobised chitosan with the general formula (I), such as described hereinabove, and optionally an α-cyclodextrin, are added to the solution;
(c) the mixture is stirred in order to form a suspension of particles of chitosan and optionally of cyclodextrin, encapsulating the antifungal agent.

Advantageously, all or a portion of the antifungal agent is then encapsulated in particles of hydrophobised chitosan and optionally of α-cyclodextrin. In particular, the antifungal agent can be encapsulated in particles comprising non-covalent inclusion complexes formed between the hydrophobised chitosan and the α-cyclodextrin.

Applications

The present invention also relates to a pharmaceutical, dermatological, dermo-cosmestic or veterinary composition comprising the composition according to the invention, in association with a pharmaceutically, dermatologically, dermo-cosmetically or veterinarily acceptable excipient.

Examples of excipients that are suitable for these embodiments include solvents, dispersion mediums, isotonic agents, absorption delaying agents, absorption promoters, lipids, proteins, peptides, sugars such as glucose or saccharose, surfactants, gelling agents, thickening agents, binding agents, diluents, preservatives, antioxidants, colouring agents, solubilizers, disintegrants, sweeteners.

According to one embodiment, the composition of the invention, the pharmaceutical, dermatological, dermo-cosmetic or veterinary composition of the invention or the drug of the invention, can be administered by parenteral route, such as for example by intramuscular, subcutaneous, intramedullary or intravenous route; by intrathecal injection, intraventricular, intraperitoneal or intraocular route; by oral, sublingual, nasal, aerosol, pulmonary, ear route; by topical, cutaneous, transdermal, ocular, rectal, vaginal route; by application on the nails; by any other route that allows for a localised administration, such as for example on a tumour or a tissue.

According to one embodiment, the composition of the invention, the pharmaceutical, dermatological, dermo-cosmetic or veterinary composition of the invention or the drug of the invention, is formulated for example according to one of the formulations chosen from the group comprising the following forms: tablet, coated tablet, gastro-resistant tablet, tablet, soft capsule, hard capsule, hard-shelled capsule; powder, pill, granule, solution, emulsion, suspension, syrup, eye drops, subgingival irrigation, mouth bath, chewing gum, toothpaste, patch, implant, suppository, paste, cream, gel, lotion, milk, ointment, spray, shampoo, varnish, plaster, catheter, compress, gauze. These formulations can be prepared by methods known to those skilled in the art.

According to one preferred embodiment, the composition of the invention, the pharmaceutical, dermatological, dermocosmetic or veterinary composition of the invention or the drug of the invention, is formulated in the form of a gel, more preferably a hydrogel. In particular, the gel can be a heat-sensitive gel, preferably a heat-sensitive hydrogel, such as for example the copolymer ((ethylene oxide)$_{97}$(propylene oxide)$_{69}$(ethylene oxide)$_{97}$) known under the name of Pluronic® F127 or poloxamer P407.

The advantageous forms in the paramedical field are plasters, catheters, compresses, gauzes, absorbent cotton, physiological serum, sprays.

The advantageous forms in the veterinary field are the oral forms (tablets, powders, soft capsules, hard capsules, hard-shelled capsules, granules, pastes, solutions, suspensions), injectable forms (solutions, suspensions), and topical forms of which the action can be local or systemic (sprays, eartags, powders, lotions, ointments, shampoos, patches, emulsions, milks, gels, creams).

The advantageous forms in the cosmetic field, preferably dermo-cosmetic field, are gels, pastes, ointments, lotions, creams, milks, sticks, shampoos, powders, aerosols, patches.

Moreover, the present invention relates to a medicament comprising a composition according to the invention.

In one embodiment, the composition of the invention is used in order to disinfect equipment or medical equipment. In one embodiment, the composition is used in order to impregnate a material or a surface.

According to another embodiment, the composition of the invention can be used for the conservation of substances, in particular substances such as for example food products, beverages, cosmetic products, personal hygiene products, home hygiene products, paints or wood.

According to another embodiment, the composition of the invention can be used in order to prevent or limit the formation of biofilms, preferably fungal biofilms. "Biofilm" refers to an organised community of cells fixed to a surface.

Antifungal Use

The present invention further relates to the use of the composition of the invention as an antifungal agent or in the treatment of fungal infections. According to one embodiment, the composition of the invention can also be used for the prevention of fungal infections.

According to one embodiment, the composition of the invention used as an antifungal agent or in the treatment of fungal infections or for the prevention of fungal infections, comprises hydrophobised chitosan with the general formula (I) and an antifungal agent, as described above. Optionally, the composition further comprises an α-cyclodextrin.

According to one particular embodiment, the composition of the invention used as an antifungal agent or in the treatment of fungal infections or for the prevention of fungal infections, comprises:
  at least one antifungal agent;
  hydrophobised chitosan with the general formula (Ia) such as previously described;
  an α-cyclodextrin, said α-cyclodextrin being in the form of a monomer, and forming with the hydrophobised chitosan with the general formula (Ia) a non-covalent inclusion complex.

According to one embodiment, the composition of the invention is used for treating a patient afflicted by a fungal infection.

"Fungal infection" refers in this invention to any infection of the skin, mucosa or appendages with yeasts (in particular by *Candida* sp.), with moulds (in particular by *Aspergillus* sp.), with dermatophytes (in particular by *Trichophyton* sp.), with dimorphic mushrooms (in particular *Histoplasma* sp) and all invasive fungal infections (deep) with yeasts, moulds or dimorphic mushrooms.

According to another embodiment, the composition of the invention is used to treat a material, in particular a woven or non-woven material, or a surface contaminated by a microorganism, preferably by a mushroom.

In particular, the composition of the invention can be used as an antifungal agent or in the treatment of fungal infections, in relation with the mushrooms selected from the group comprising *Candida albicans, Aspergillus fumigatus*, dermatophytes, dimorphic mushrooms and a protozoan sensitive to antifungals *Leishmania* sp., preferably *Leishmania major*.

In one embodiment, the hydrophobised chitosan with the formula (I), preferably the hydrophobised chitosan with the formula (I) in the form of particles (including the inclusion complex particles formed from hydrophobised chitosan with the formula (I) and from cyclodextrin), have antifungal properties.

In one particular embodiment, the composition of the invention has a synergistic activity with respect to the activity of the antifungal agent and hydrophobised chitosan with the formula (I), preferably hydrophobised chitosan with the formula (I) in the form of particles (including the inclusion complex particles formed from hydrophobised chitosan with the formula (I) and from cyclodextrin).

"Synergistic activity" refers in this invention to the interaction of two or several agents acting together positively so as to produce an effect that they cannot produce alone.

In particular, the synergy can be evaluated according to the method recommended since 2003 by the ASM (American Society for Microbiology) and described by Odds (Odds F. C., *J. Antimicrobial Chemotherapy*, 2003, 52, 1).

According to another particular embodiment, the composition of the invention has an additive activity with respect to the activity of the antifungal agent and hydrophobised chitosan with the formula (I), preferably hydrophobised chitosan with the formula (I) in the form of particles (including the inclusion complex particles of hydrophobised chitosan with the formula (I) and from cyclodextrin).

An "additive activity", during the simultaneous use of several agents, corresponds to the sum of the activities of each agent alone.

In one embodiment, the quantity of antifungal agent used in the composition of the invention in order to obtain an antifungal effect is less than the quantity usually used for said antifungal agent. The possibility of using low quantities of antifungal agent is an advantage of the composition of this invention.

According to one embodiment, the antifungal composition of the invention can be administered alone or in combination with an active agent, such as for example an antimicrobial, an antibiotic, an antifungal, an antiseptic.

In one embodiment, the antifungal composition of the invention is used in order to disinfect equipment or medical equipment. In one embodiment, the composition is used in order to impregnate a material or a surface.

According to another embodiment, the antifungal composition of the invention can be used for the conservation of substances, in particular substances such as for example food products, beverages, cosmetic products, personal hygiene products, home hygiene products, paints or wood.

According to another embodiment, the antifungal composition of the invention can be used in order to prevent or limit the formation of biofilms, preferably fungal biofilms. "Biofilm" refers to an organised community of cells fixed to a surface.

Antiparasitic Use

This invention further relates to a composition of the invention for use as an antiparasitic agent or in the treatment of parasitic infections. According to one embodiment, the composition of the invention can also be used for the prevention of antiparasitic infections.

According to one embodiment, the composition of the invention for use as an antiparasitic agent or in the treatment of parasitic infections or for the prevention of parasitic infections, comprises hydrophobised chitosan with the general formula (I) such as is described above. Optionally, the composition further comprises an α-cyclodextrin. Optionally, the composition further comprises an antifungal agent, such as described in this application.

According to one particular embodiment, the composition of the invention for use as an antiparasitic agent or in the treatment of parasitic infections or for the prevention of parasitic infections, comprises:
hydrophobised chitosan with the general formula (Ia) such as previously described;
an α-cyclodextrin, said α-cyclodextrin being in the form of a monomer, and forming with the hydrophobised chitosan with the general formula (Ia) a non-covalent inclusion complex.

According to another particular embodiment, the composition of the invention for use as an antiparasitic agent or in the treatment of parasitic infections or for the prevention of parasitic infections, comprises:
hydrophobised chitosan with the general formula (Ib) such as previously described;
optionally an α-cyclodextrin, said α-cyclodextrin being in the form of a monomer, and when it is present, the α-cyclodextrin forms with the hydrophobised chitosan with the general formula (Ib) a non-covalent inclusion complex.

According to another particular embodiment, the composition of the invention for use as an antiparasitic agent or in the treatment of parasitic infections or for the prevention of parasitic infections, comprises hydrophobised chitosan with the general formula (Ib) such as previously described.

According to one embodiment, the composition of the invention is for use in the treatment of a patient afflicted by a parasitic infection.

"Parasitic infection" refers in this invention to any infection by a parasite, in particular by a *Leishmania*, in particular *Leishmania major*, *Leishmania tropica*, *Leishmania braziliensis*, *Leishmania aethiopica*, *Leishmania mexicana*, *Leishmania donovani*, *Leishmanoa guyanensis*, *Leishmania panamensis*, *Leishmania infantum*; by a *Trichomonas*, in particular *Trichomonas vaginalis*; or by a *Trypanosome*, in particular *Trypanosoma avium*, *Trypanosoma brucei*, *Trypanosoma gambiense*, *Trypanosoma rhodesiense*, *Trypanosoma cruzi*, *Trypanosoma congolense*, *Trypanosoma equinum*, *Trypanosoma equiperdum*, *Trypanosoma evansi*, *Trypanosoma lewisi*, *Trypanosoma melophagium*, *Trypanosoma percae*, *Trypanosoma rangeli*, *Trypanosoma rotatorium*, *Trypanosoma simiae*, *Trypanosoma suis*, *Trypanosoma theileri*, *Trypanosoma triglae*, *Trypanosoma vivax*.

According to another embodiment, the composition of the invention is used to treat a material, in particular a woven or non-woven material, or a surface contaminated by a parasite.

In particular, the composition of the invention can be used as an antiparasitic agent or in the treatment of parasitic infections, in relation with the parasites selected from the group comprising *Leishmania*, in particular *Leishmania major*, *Leishmania tropica*, *Leishmania braziliensis*, *Leishmania aethiopica*, *Leishmania mexicana*, *Leishmania donovani*, *Leishmanoa guyanensis*, *Leishmania panamensis*, *Leishmania infantum*; *Trichomonas*, in particular *Trichomonas vaginalis*; or *Trypanosome*, in particular *Trypanosoma avium*, *Trypanosoma brucei*, *Trypanosoma gambiense*, *Trypanosoma rhodesiense*, *Trypanosoma cruzi*, *Trypanosoma congolense*, *Trypanosoma equinum*, *Trypanosoma equiperdum*, *Trypanosoma evansi*, *Trypanosoma lewisi*, *Trypanosoma melophagium*, *Trypanosoma percae*, *Trypanosoma rangeli*, *Trypanosoma rotatorium*, *Trypanosoma simiae*, *Trypanosoma suis*, *Trypanosoma theileri*, *Trypanosoma triglae*, *Trypanosoma vivax*.

In one embodiment, the hydrophobised chitosan with the formula (I), preferably the hydrophobised chitosan with the formula (I) in the form of particles (including the inclusion complex particles formed from hydrophobised chitosan with the formula (I) and from cyclodextrin), has antiparasitic properties.

According to one embodiment, the antiparasitic composition of the invention can be administered alone or in combination with an active agent, such as for example an antimicrobial, an antibiotic, an antifungal, an antiseptic.

EXAMPLES

Figure 1:
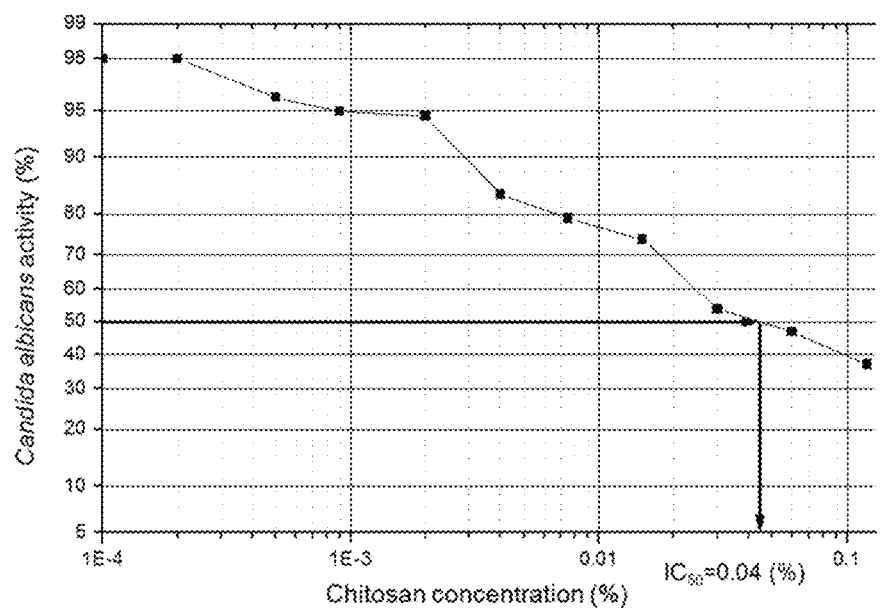
FIG. 1 is a graph representing the viability of *Candida albicans* in function of the concentration in hydrophobised chitosan, for the determination of the $IC_{50}$ of hydrophobised chitosan against *Candida albicans*.

This invention shall be understood better when reading the following examples which illustrate the invention in a non-limiting manner.

Abbreviations

PA: palmitic acid
OA: oleic acid
CD: cyclodextrin
$CDCl_3$: deuterated chloroform
$IC_{50}$: inhibitory concentration 50
MC: modified chitosan
$D_2O$: heavy water
Da: molar weight unit in dalton, which corresponds to g/L
DCl: deuterated hydrochloric acid
DDA: degree of deacetylation
DMSO-d6: deuterated dimethylesulfoxide
DS: degree of substitution
EDCI: 1-ethyl-3-(3-dimethylaminopropyl) carbodiimide
IBCA: isobutylcyanoacrylate
IR: infrared
kDa: kilodalton
kHz: kilohertz
$M_m$: molar weight
MOPS: 3-(N-morpholino)propanesulfonic acid
MTT: (3-(4,5-dimethylthiazol-2-yl)-2,5-diphenyltetrazolium) bromide
MHz: Megahertz
PIBCA: poly(isobutylcyanoacrylate)
NMR: nuclear magnetic resonance
δ: displacement of the proton, expressed in ppm
Material and Methods $^1$H-NMR:

The $^1$H-NMR spectra were carried out on a Bruker ARX spectrometer, 300 MHz or 500 MHz. Solvents: heavy water ($D_2O$) with 1% v/v of DCl, deuterated chloroform ($CDCl_3$), deuterated dimethylesulfoxide (DMSO-d6). The spectra are obtained at ambient temperature with an electromagnetic field of 300 MHz. When the acylated polysaccharide is sparingly soluble or when the viscosity is high, the samples can be heated until 85° C. and the spectra are obtained via an electromagnetic field of 500 MHz.

$^{13}$C-NMR of the Solid:

The $^{13}$C-NMR spectra of the solid were carried out on an AVANCE II BRUKER spectrometer. Specialised NMR techniques of the solid were used, in particular magic angle spinning (MAS) and polarisation transfer from $^1$H to $^{13}$C (CP) in order to avoid the disadvantages linked to relaxation times which are sometimes very long in solid state. The measurements were taken at ωL=500 MHz ($^1$H) and 125.77 MHz ($^{13}$C); the contact time $^1$H/$^{13}$C set to 1.5 ms. The samples are spun at the magic angle at a frequency of 10 kHz, using a 4 mm rotor.

IR Spectra:

The IR spectra were carried out on a FT/IR-4100 spectrometer, JASCO (ATR-FTIR).

Transmission Electron Microscopy:

Transmission electron microscopy (TEM) was used to observe the microparticles and nanoparticles using a Jeol 1400 60 kV microscope and a camera.

TEM was also carried out using a Philips EM208 microscope and an AMT camera at the CCME of Orsay (Joint Centre for Electron Microscopy), France. The preparations are diluted to 1/100 in MilliQ® water. 3 µL of these dilutions are deposited onto a copper grid with a Formvar-Carbon membrane. After 5 min, a drop of aqueous solution at 1% of phosphotungstic acid is deposited. After 30 seconds, the excess liquid is removed and the sample is observed under the microscope.

Particle Size:

The size of the particles was evaluated by measuring the hydrodynamic diameter. The measurements of the average hydrodynamic diameters of the nanoparticles and microparticles were carried out at 25° C., with a Zetasizer nanoseries Nano-ZS90 from Malvern instruments SA (Orsay, France) by quasi-elastic light scattering. The samples were diluted beforehand by sampling 30 µL of suspension of nanoparticles or microparticles and by diluting them in 1 mL of MilliQ® water. The temperature is balanced for 5 min before measuring. The average hydrodynamic diameter is obtained using three repeated measurements on three independent dilutions. The hydrodynamic diameters of the microparticles were also measured by a laser particle sizer (MasterSizer 2000) from Malvern instruments SA (Orsay, France). Moreover, the diameter observed in TEM was measured using the ImageJ software. The diameter of 50 nanoparticles is measured for each preparation.

Quantity of Sulphur:

The quantity of sulphur in the preparations is determined by elementary analysis using a LECO SC144 Analyser (Central analysis department of the CNRS, Solaize, France). 10 mg of lyophilised sample are heated to 1350° C. under a flow of oxygen and the $SO_2$ is detected by infrared.

Zeta Potential:

The ζ potential of the particles is measured at 25° C. using the Zetasizer nanoseries Nano-ZS (Malvern Instruments, France). 60 µL of each preparation is diluted in 2 mL of a solution of NaCl 1 mM filtered beforehand (Millipore Millex-HV Hydrophilic PVDF 0.22 µm filter). The average ζ potential is obtained using three repeated measurements on three independent dilutions.

Lyophilisation:

Certain derivatives were lyophilised using an Alpha 1-2 lyophilizer (Avantec, France), for 48 hours after having frozen the solutions for at least 12 hours.

Products:

The chlorhexidine digluconate was obtained from INRESA, Bartenheim, France. The Fungizone® was obtained from Bristol Myers Squibb. The anhydrous dimethylformamide, dichloromethane, diethyl ether, ethanol, methanol, ammonia, glacial acetic acid (98% (m/m)) come from VWR, France. The N-(3-dimethylaminopropyle)-N-ethylcarbodiimide chloride (EDCI), palmitic acid (99% (m/m)), oleic acid (>98% (m/m)), sodium bicarbonate, sodium hydroxide, sodium chloride, sodium nitrite ($NaNO_2$), methanesulfonic acid, palmitoyl chloride, oleoyl chloride, heavy water, deuterated hydrochloric acid (DCl), deuterated chloroform ($CDCl_3$), deuterated dimethylesulfoxide (DMSO-$d_6$), anhydrous pyridine, triethylamine, RPMI 1640, MOPS, MTT, menadione were supplied by Sigma-Aldrich Chemical Co, Saint-Quentin Fallavier, France. The IBCA (isobutylcyanoacrylate, lot 3138/3) comes from Henckel Biomedical® (Dublin, Ireland). The ceric ammonium nitrate(IV) (lot 380955/1) was obtained from Fluka® (Saint-Quentin-Fallavier, France). The Pluronic F68 or poloxamer 188 (lot 52-0791) comes from BASF® (Germany). The sodium hydroxide (lot 0400182), sodium chloride (lot N293), acetic acid IN (lot 93067) and hydrochloric acid 37% (lot 92073) were supplied by Prolabo® (France). The acetonitrile (grade HPLC, lot V8D944248D), as well as the glacial acetic acid (lot 1A156051C) come from Carlo Erba®. The nitric acid 63% (lot A018814601) was obtained from Acros Organics® (New Jersey, USA). The sodium nitrite $NaNO_2$ (lot 42K3485) comes from Sigma®. The Traut (2-iminothiolane HCl) reagent was synthesized by the organic chemistry department (Biocis UMR CNRS 8076) of the School of Pharmacy of Paris XI (Châtenay-Malabry, France).

Chitosan of average viscosity and of molar weight $M_m$=250 kDa, was supplied by Sigma-Aldrich Chemical Co, Saint-Quentin Fallavier, France.

The other chitosans (20 and 145 kDa) were obtained, unless mentioned otherwise, after depolymerisation of the chitosan commercial $M_m$=250 kDa according to the technique developed by Huang and al (*Pharmaceutical Research,* 2004, 21(2), 344): 2 g of chitosan commercial are solubilised overnight in 100 mL of acetic acid (6% v/v), this solution of chitosan is then depolymerised by chemical reaction for 1 h with 10 mL of $NaNO_2$ (85 mg/mL). The depolymerised chitosan is then precipitated by increasing the pH to 9 using a solution of sodium hydroxide (4 mol/L) and recovered by filtration (sintered-glass filter no. 4, in a vacuum). It is then solubilised in 20 mL of acetic acid (0.1 mol/L) and dialysed (dialysis membrane Spectra/Por, MWCO 3500, lot 3228543, Spectrum Laboratories Inc®) against 1 L of distilled water twice for 1 h30 then overnight then lyophilised.

The molar weight of the depolymerised chitosan is determined by capillary viscosimetry. The flow time (t) in a microtube µ-Ubbelohde (type 53710/I, no. 1016187, R=0.01022 $mm^2/s^2$, Schott Geräte) of solutions of chitosan in a mixture of 0.1 mol/L acetic acid and 0.2 mol/L NaCl at different concentrations (c=0.25/0.50/1.00/1.50/2.00 g/L) is measured at 20° C. (bath CT1450 Schott Geräte and cooling system CK100 Schott Geräte) using an AVS400 viscometer (Schott Geräte). For each concentration, the equilibration time is 5 min and five successive measurements are taken. Using the results obtained the intrinsic viscosity [η] is deduced by taking the ordinate at the origin of the line $$\frac{t - t_0}{t_0 C} = f(C)$$

with $t_0$ the flow time of the mixture of 0.1 mol/L acetic acid and of 0.2 mol/L NaCl. The molar weight is then calculated by using the equation of Mark-Houwink-Sakurada $\eta = KM_w^a$, with K=1.81.$10^{-6}$ and a=0.93.

1. Synthesis of Hydrophobised Chitosans

Hydrophobised chitosans were synthesised in order to be used in the compositions of the invention. In particular, chitosans were hydrophobised by N- or O-acylation in the presence of fatty acids. Chitosans have also been hydrophobised by functionalisation by a poly(alkylcyanoacrylate). Before hydrophobisation, certain chitosans were modified by groups substituted by a thiol function.

1.1. N-Acyl Chitosan

Preparation 1 g of chitosan ($M_m$=20, 145 or 250 kDa), of which the degree of deacetylation (DDA) is equal to 85%, is dissolved in an aqueous solution of acetic acid at 1% v/v (100 mL) diluted with methanol (75 mL). The oleic acid or palmitic is dissolved in 10 mL of methanol and added to the solution of chitosan. A number of moles of EDCI equal to that of the fatty acid, is added drop by drop to the fatty acid and chitosan mixture under continuous magnetic stirring. After 24 hours, the product is precipitated in a methanol/ammonia 7/3 v/v mixture. The precipitate is filtered on a sintered-glass filter and washed successively with water, methanol then diethyl ether. Finally, the product is vacuum dried for 48 hours.

This method makes it possible to obtain different types of N-acyl chitosan according to the type of fatty acid used, the rate of grafting (degree of substitution) and the molar weight of the chitosan.

Infrared Analysis

Chitosans hydrophobised by N-acylation were analysed by IR spectroscopy. The comparison with the spectrum of the starting chitosan confirms the formation of the amide bond.

NMR $^1$H Analysis

For the characterisation of the N-acyl chitosan by NMR of the proton, a solution at a concentration equal to 5 g/L is prepared in heavy water ($D_2O$) in the presence of deuterated hydrochloric acid (DCl). This step allows for the exchanging of the labile protons of the hydroxyl groups with deuterium atoms. The labile protons of the hydroxyl groups all resonating at the same frequency, exchanging them with deuterium atoms makes it possible to eliminate the residual signal of the light water. So as to decrease the viscosity, the experiments were recorded at a temperature of 85° C. with a number of acquisitions and a relaxation delay of 5 and 1 seconds respectively.

The NMR spectra of the proton of the chitosans hydrophobised by N-acylation have an additional signal with respect to the spectrum of non-hydrophobised chitosan at δ=1.017 ppm. It corresponds to the signal of the methyl group at the end of the fatty acid chain, confirming the grafting.

Characteristics of the Chitosans Hydrophobised by N-Acylation MC1-MC9

The characteristics of the hydrophobised chitosans MC1-MC9 are grouped together in table 1 hereinbelow. The degree of substitution was calculated using the results of the elementary analysis of the N-acyl chitosan and native chitosan.

TABLE 1

Characteristics of the N-acyl chitosans.

| Modified chitosan | Grafted fatty acid | $M_m$ Chitosan used (kDa) | Degree of substitution (%) |
|---|---|---|---|
| MC1 | Oleic acid | 250 | 1.19 |
| MC2 | Oleic acid | 250 | 1.67 |
| MC3 | Oleic acid | 250 | 7.43 |
| MC4 | Oleic acid | 145 | 13.47 |
| MC5 | Oleic acid | 20 | 5.61 |
| MC6 | Oleic acid | 20 | 6.35 |
| MC7 | Palmitic acid | 250 | 0.55 |
| MC8 | Palmitic acid | 250 | 13.12 |
| MC9 | Palmitic acid | 250 | 17.01 |

1.2. O-Acyl Chitosan
Preparation

The chitosan (250 kDa, 2 g) is dissolved in 20 mL of methanesulfonic acid, at ambient temperature under continuous magnetic stirring, for one hour. The chloride acid (oleic or palmitic) is then introduced into the reaction medium. After 5 hours, the mixture is cooled in an ice bath in order to stop the reaction, a precipitate is formed. The precipitate is dialysed for 12 hours, then neutralised using sodium bicarbonate. It is then dialysed for 48 hours and lyophilised.

This method makes it possible to obtain different types of O-acyl chitosan according to the type of fatty acid chloride used, the rate of grafting (degree of substitution) and the molar weight of the chitosan.

Infrared Analysis

Chitosans hydrophobised by O-acylation were analysed by IR spectroscopy. The comparison with the spectrum of the starting chitosan confirms the presence of the fatty acid alkyl chains.

NMR $^1$H Analysis

The NMR spectra of the proton of the chitosans hydrophobised by O-acylation have additional peaks with respect to the spectrum of non-hydrophobised chitosan: those characteristic of the CH3 group at the end of the chain at 0.88 ppm and of the proton of the methylene CH2 groups in the vicinity of the CO function at 2.8 ppm.

Characteristics of the Chitosans Hydrophobised by O-Acylation MC10-MC12

The characteristics of the hydrophobised chitosans MC10-MC12 are grouped together in table 2 hereinbelow. The degree of substitution was calculated using the results of the elementary analysis of the O-acyl chitosan and of the native chitosan.

TABLE 2

Characteristics of the O-acyl chitosans.

| Modified chitosan | Grafted fatty acid | $M_m$ Chitosan used (kDa) | Degree of substitution (%) |
|---|---|---|---|
| MC10 | Oleic acid | 250 | 1.41 |
| MC11 | Palmitic acid | 250 | 2.25 |
| MC12 | Palmitic acid | 250 | 4.64 |

1.3. Thiolation of the Chitosan

According to certain aspects of the invention, the hydrophobised chitosan comprises groups functionalised by a thiol. The introduction of these groups can be carried out in the chitosan, before grafting hydrophobic groups.

The thiolation of the chitosan, in particular of the depolymerised chitosan, can be carried out according to the technique developed by Bernkop-Schnürch et al. (*International Journal of Pharmaceutics*, 2003, vol. 260, no. 2, p. 229-237.): 1 g of depolymerised chitosan is solubilised in 100 mL of acetic acid (1% m/v), the pH is adjusted to 6.5 using a solution of NaOH 1 N then the Traut reagent is added in the proportions chitosan/2-iminothiolane: 5/2 (m/m). After 24 h of reaction at ambient temperature and under magnetic stirring, the chitosan-4-thiol-butylamidine (chitosan-TBA) obtained is dialysed (dialysis membrane Spectra/Por, MWCO 3500) 8 h against 5 L of HCl 5 mM, twice 8 h against 5 L of HCl 5 mM/1% NaCl, 8 h against 5 L of HCl 5 mM and 8 h against 5 L of HCl 1 mM. Chitosan-TBA is lyophilised for 48 h (lyophiliser SMH15, Usifroid Procédés Rieutord, Maurepas, France).

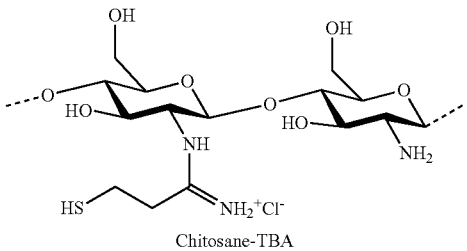

Chitosane-TBA

Chitosan-TBA can then be grafted by hydrophobic groups by N- or O-acylation as described hereinabove. Chitosan-TBA can also be hydrophobised by functionalisation by a poly(alkylcyanoacrylate) (cf. hereinbelow).

Note: When the chitosan used for the thiolation has a molar weight of 20 kDa ("chitosan20"), the product obtained is noted as "chitosan20-TBA".

1.4. Chitosan Functionalised by a Poly(Alkylcyanoacrylate)

Chitosan was hydrophobised by functionalisation by a poly(alkylcyanoacrylate), poly(isobutylcyanoacrylate) (PIBCA). The chitosan used for the hydrophobisation is a mixture of depolymerised chitosan 20 kDa ("chitosan20") and of chitosan-TBA obtained as described hereinabove ("chitosan20-TBA").

The PIBCA-[chitosan/chitosan-TBA] obtained has the form of particles.

The functionalisation by the PIBCA can be carried out by radical emulsion polymerisation or by emulsion anionic polymerisation.

1.4.1. Preparation by Radical Emulsion Polymerisation
Preparation

Nanoparticles PIBCA-[chitosan20/chitosan20-TBA] are prepared by radical emulsion polymerisation (I. Bravo-Osuna et al., *Biomaterials*, 2007, vol. 28, no. 13, p. 2233-2243; C. Chauvierre et al., *Macromolecules*, 2003, vol. 36, no., p. 6018-6027): 0.069 g of chitosan 20 kDa/chitosan (20 kDa)-TBA 75/25 (% m/m) are dissolved in 4 mL of nitric acid 0.2 M. From 0 to 4% (m/v) of Pluronic F68 is then dissolved in this solution. The solution is placed in a bath at 40° C. under magnetic stirring (Bioblock AM3001K plate). After 10 min of argon bubbling, the magnetic stirring is increased (1000 rpm) in such a way as to form a vortex, then 1 mL of solution of ceric ammonium nitrate (IV) ($8 \cdot 10^{-2}$ M in the nitric acid 0.2 M) and 250 µL of IBCA are added afterwards. The argon bubbling is maintained for a further 10 min then the reaction continues for 50 minutes. The preparation is then cooled 5 min in crushed ice.

The nanoparticles are purified by dialysis (dialysis membrane Spectra/Por, MWCO 100,000, Spectrum laboratories Inc.®) against 1 L of a solution of acetic acid 16 µM twice 30 min, twice 1 h then overnight. The volume of the preparations is adjusted to 8 mL with MilliQ® water.

Size of the Nanoparticles

Table 3 shows that all of the nanoparticles obtained are of nanometric size and that the presence of Pluronic F68 in the polymerisation medium during the preparation of nanoparticles makes it possible to decrease their hydrodynamic diameter ($D_h$).

TABLE 3

Physical-chemical characterisations of the nanoparticles of PIBCA-[chitosan20/chitosan20-TBA] 75/25% m/m obtained by radical emulsion polymerisation according to the initial percentage of Pluronic F68 present in the polymerisation medium (0, 1, 2, 3 and 4%).

| Sample code | $D_h$ (nm) | ζ Potential (mV) | Concentration of groups - SH[a] (mol/mg) |
|---|---|---|---|
| Np 0% | 206 ± 2 | +38 | 1.79 |
| Np 1% | 134 ± 2 | +31 | 0.58 |
| Np 2% | 101 ± 1 | +23 | 0.21 |
| Np 3% | 93 ± 2 | +14 | 0.06 |
| Np 4% | 68 ± 1 | +12 | 0.03 |
| Np Control[b] | 103 ± 3 | −7 | 0 |

[a]iodo titration,
[b]nanoparticles of PIBCA not covered with chitosan stabilised with the Pluronic F68.

ζ Potential of the Nanoparticles

Table 3 shows that the nanoparticles PIBCA-[chitosan/chitosan-TBA] 75/25% m/m are positively charged. This is due to the presence on their surface of a crown of chitosan which is a positively charged polymer (amine functions). On the contrary the control nanoparticles that do not have a crown of chitosan are negatively charged.

The nanoparticles prepared without Pluronic F68 have a ζ potential of about +38 mV. The presence of Pluronic F68 during the preparation of nanoparticles decreases the ζ potential of the nanoparticles: it changes from +38 mV to +12 mV respectively for a percentage from 0 to 4% of Pluronic F68, we therefore see that the surface properties of the nanoparticles have been modified.

Dosage of Sulphur

Table 3 also shows the results of the dosage of sulphur. The presence of Pluronic F68 decreases the total quantity of sulphur in the preparation (from 0.86% to 0.77% (m/m) respectively for 0 and 4% of Pluronic F68 (m/v)) resulting in a modification of the surface properties of the nanoparticles. These results could be explained by a competition between the chitosan-TBA which carries the sulphur groups and the Pluronic F68 during the polymerisation.

1.4.2. Preparation by Emulsion Anionic Polymerisation

Preparation

Nanoparticles PIBCA-[chitosan20/chitosan20-TBA] are prepared by emulsion anionic polymerisation according to the method of Bravo-Osuna and al (I. Bravo-Osuna and al, Int. J. Pharm. 316(1-2) (2006) 170-175): 0.069 g of chitosan 20 kDa/chitosan (20 kDa)-TBA 75/25% m/m are dissolved in 5 mL of nitric acid 0.2 M. The solution is placed in a bath at 40° C. under magnetic stirring (Bioblock AM3001K plate). After 10 min of argon bubbling, the magnetic stirring is increased (1000 rpm) in such a way as to form a vortex 250 µL of IBCA are added afterwards. The argon bubbling is maintained for a further 10 min then the reaction continues for 50 minutes. The preparation is then cooled 5 min in crushed ice.

The nanoparticles are purified by dialysis as described above.

Various ratios of chitosan20/chitosan20-TBA were implemented (100/0, 75/25, 50/50, 25/75 and 0/100% m/m).

Physical-Chemical Characterisations

Table 4 shows that the particles obtained are of nanometric size and are positively charged.

TABLE 4

Physical-chemical characterisations of the nanoparticles of PIBCA-[chitosan20/chitosan20-TBA] 75/25% m/m and 100/0% m/m obtained by emulsion anionic polymerisation.

| Formulations | $D_h$ (nm) | ζ potential (mV) |
|---|---|---|
| PIBCA/(Chito20/Chito20-TBA) 100/0% m/m | 195 ± 9 | +43.6 ± 0.3 |
| PIBCA/(Chito20/Chito20-TBA) 75/25% m/m | 127 ± 1 | +27.1 ± 0.2 |

2. Particles of Hydrophobised Chitosan and of Cyclodextrin

Microparticles and nanoparticles were formed using α-cyclodextrin and hydrophobised chitosan by fatty acids, obtained as described in the example 1.1 and 1.2. The hydrophobised chitosans used for forming the particles are listed in table 3 hereinbelow.

The α-cyclodextrin as well as the 0- or N-acyl chitosan are weighed in a small bottle. Distilled water is then added and the mixture is maintained under magnetic stirring for 3 days.

The characteristics of the particles formed are presented in table 5.

TABLE 5

Particle sizes obtained using N-acyl or O-acyl chitosan.

| Modified chitosan | % m chitosan amphiphilic | % m of α-CD | % m water | Particle size (nm)* |
|---|---|---|---|---|
| MC8 | 1.0 | 10.0 | 89.0 | 7320 ± 1823 |
| MC12 | 1.0 | 10.0 | 89.0 | 2090 ± 367 |
| MC9 | 2.5 | 10.0 | 87.5 | 1416 ± 45 |
| MC3 | 1 | 10 | 89.0 | 1662 ± 24 |

*Hydrodynamic diameter expressed in volume.

3. Compositions of the Invention

Compositions according to this invention were prepared.

Composition 1: association of Fungizone® and of particles of hydrophobised chitosan and of cyclodextrin.

| Compounds | Type | Concentration |
|---|---|---|
| Fungizone ® | antifungal agent | 0.5% m/v |
| MC3 | hydrophobised chitosan | 1% m/v |
| α-cyclodextrin | cyclodextrin | 10% m/v |

Composition 2: association of Chlorhexidine and of particles of hydrophobised chitosan and of cyclodextrin.

| Compounds | Type | Concentration |
|---|---|---|
| chlorhexidine digluconate | antifungal agent | 0.5% m/v |
| MC3 | hydrophobised chitosan | 1% m/v |
| α-cyclodextrin | cyclodextrin | 10% m/v |

Compositions 1 and 2 were prepared using particles of hydrophobised chitosan MC3 and of cyclodextrin in water, as described in paragraph 2 hereinabove. The antifungal agent (Fungizone® or chlorhexidine digluconate) is then added.

Composition 3: encapsulation of Fungizone® in particles of hydrophobised chitosan and of cyclodextrin.

| Compounds | Type | Concentration (% m/v) |
|---|---|---|
| Fungizone ® | antifungal agent | 0.5% m/v |
| MC3 | hydrophobised chitosan | 1% m/v |
| α-cyclodextrin | cyclodextrin | 10% m/v |

Composition 3 was prepared by dissolving the antifungal agent in water then by adding the hydrophobised chitosan and the cyclodextrin. The mixture is maintained under magnetic stirring for 3 days. The concentration in antifungal agent that was not encapsulated can be determined by dosage in the supernatant of the preparation.

Composition 4: composition comprising particles of hydrophobised chitosan and of cyclodextrin.

| Compounds | Type | Concentration (% m/v) |
|---|---|---|
| MC3 | hydrophobised chitosan | 1% m/v |
| α-cyclodextrin | cyclodextrin | 10% m/v |

Composition 4 was prepared using particles of hydrophobised chitosan MC3 and of cyclodextrin in water, as described in paragraph 2 hereinabove.

Compositions 5a to 5d: compositions comprising hydrophobised chitosan by PIBCA.

| | Concentration (% m/m) | | | |
|---|---|---|---|---|
| Compounds | 5a | 5b | 5c | 5d |
| PIBCA-chitosan20 | 100 | 75 | 50 | 25 |
| PIBCA-chitosan20-TBA | 0 | 25 | 50 | 75 |

Compositions 5a to 5d were prepared as described in paragraph 1.4.2 hereinabove.

4. Antifungal Activity of the Compositions According to the Invention

The antifungal activity of the compositions of the invention was studied on *Candida albicans*. In particular, compositions comprising an association of particles of hydrophobised chitosan and of cyclodextrin, such as described in the example 2, and of chlorhexidine digluconate or Fungizone® as antifungal agents, have been tested.

A comparison of the antifungal activity of the compositions of the invention was carried out with the antifungal activity of the constituents taken individually. Additive or synergistic effects were shown for the compositions of the invention.

4.1. Material
Inoculum

The inoculum is prepared by sampling 5 colonies obtained after 24 h of culture on Sabouraud agar medium, each one of at least 1 mm in diameter, and by putting them in suspension in 5 mL of sterile NaCl (0.85%). The turbidity of each suspension is evaluated by measuring the optical density at a wavelength of 530 nm then adjusted with a sterile isotonic solution so as to obtain an absorbance equivalent to that obtained with the turbidimetric standard (Mac Farland 0.5).

This protocol leads to the obtaining of a suspension of which the concentration is between $1 \times 10^6$ and $5 \times 10^6$ CFU/mL. This suspension is then diluted to 1/1000 with the culture medium in order to have a final concentration from $0.5 \times 10^3$ to $2.5 \times 10^3$ CFU/mL.

A suspension of *Candida albicans* was prepared in the conditions described hereinabove.

Culture Medium

The culture medium used for the tests is RPMI 1640 without bicarbonate, 0.2% of glucose, buffered to pH7 by MOPS (0.165M).

4.2. Methods

Method of Measuring the Growth of Yeasts

Measuring the growth of yeasts is carried out by a standard colorimetric technique that makes use of tetrazolium salt MTT (5 mg/mL) (3-(4,5-dimethylthiazol-2-yl)-2,5-diphenyl tetrazolium bromide) with menadione (vitamin K). The tetrazolium ring of the MTT is reduced in formazan, by the mitochondrial succinate dehydrogenase of active living cells. This forms a precipitate in the culture medium of violet colour. The quantity of precipitate formed is proportional to the quantity of living cells and to the metabolic activity of each cell. It is sufficient therefore after the incubation of the cells with MTT for 1 h at 37° C., to add an agent solubilising the crystals of formazan, to centrifuge the 96-well plates, and to read the optical density of the supernatant. A simple dosage of the optical density at 570 nm by spectroscopy makes it possible to know the relative quantity of living cells.

Measurements of $IC_{50}$

Measurements of the inhibitory concentrations 50% ($IC_{50}$) are determined according to the American method approved by the National Committee for Clinical Laboratory Standards M27-A3, by microdilution in a 96-well plate (Susceptibility test methods: yeast and filamentous fungi. Johnsona et al., in Manual of Clinical Microbiology, 2011, Vol 2, p 2020-2037, ASM press Washington D.C.).

Calculation of the Association Effect: Synergy, Additive Effect, Antagonism?

The effect of the association of the chlorhexidine digluconate or of Fungizone® with the particles of hydrophobised chitosan in the compositions of the invention is determined using the calculation of the FICI ("fractional inhibitory concentration index") according to the method of Odds (Odds. F. C. Synergy, antagonism, and what the chequerboard puts between them. *Journal of Antimicrobial Chemotherapy*, 2003, 52, 1).

In order to determine the effect of the association of two molecules A and B, the method of Odds comprises the following steps:

(1) Determining the $IC_{50}$ of each molecule alone: $IC_{50}^A$ and $IC_{50}^B$;

(2) Determining the following association ratios:
   A/B=5/0 (molecule A alone); 4/1; 3/2; 2/3; 1/4; 0/5 (molecule B alone);

(3) Calculating the maximum concentration for each one of the two molecules in such a way that the $IC_{50}$ is at the centre of 6 two-fold dilutions, which reverts to choosing as a "top concentration", the $IC_{50} \times 4$;

(4) Calculating each one of the concentrations by taking into account the shares of each one of the molecules for each combination;

(5) For each one of the associations, making 6 two-fold dilutions (or 6 successive dilutions at 1/2). Then, determining the $IC_{50}$ of each one of the 4 associations;

(6) Calculating the fractional inhibitory concentrations (FIC) for each combination:

$FIC_A = [IC_{50}$ of the molecule A when mixed with the molecule $B]/[IC_{50}^A]$ $FIC_B = [IC_{50}$ of the molecule B when mixed with the molecule $A]/[IC_{50}^B]$ (7) Calculating the sum of the FIC for each combination: $\Sigma FIC = FIC_A + FIC_B$;
(8) Calculating the fractional inhibitory concentration index (FICI):

$FICI = \Sigma FIC/4$ (i.e. average of the $\Sigma FIC$ of the 4 associations).

According to the value of the FICI, it is possible to determine if there is a synergistic, additive or antagonistic effect:

FICI<0.5: synergy;
0.5<FICI<4: additive effect;
FICI>4: antagonism.

4.3. Activity of Particles of Hydrophobised Chitosan Against *Candida albicans*

Protocol

The test is carried out in a 96-well dilution microplate (8 lines A-H, 12 columns). 200 µl of culture medium are added to the 8 wells of the first column (1) and only 100 µl in the wells of the other columns (from 2 to 12).

The suspension of particles of hydrophobised chitosan MC3 prepared according to the conditions described in the example 2 (cf. table 5) is added to the well of column 1. The concentration of the hydrophobised chitosan in the suspension of particles is 1% m/v.

The cascade dilution technique of the wells of column 1 is used in such a way as to have at each time a dilution at 1/2 by passing from one well to the other until column 12 is reached.

100 µL of suspension of *Candida albicans* (inoculum) are added to each well. The concentration of the hydrophobised chitosan in the wells of the column 1 is 0.12%. The dilution microplate is incubated at 35° C. for 24 h.

The control consists in proceeding in the same way but without adding the suspension of hydrophobised chitosan.

The percentage of viability of *Candida albicans* is evaluated by using the test with MTT described hereinabove. In each well are added 10 µL of solution of MTT at a concentration of 5 mg/mL and 10 µL of Menadione at a concentration of 1.72 mg/mL. The plate is incubated for 1 h at 35° C. The microplate is centrifuged at 1000 rpm for 10 minutes. After centrifugation 100 µL of the supernatant is sampled and the optical density determined by reading the spectrophotometer at 570 nm.

The test was carried out at least three times using different cultures on agar of the strain of *Candida albicans*.

Results

The results of the activity of the particles of hydrophobised chitosan against *Candida albicans* are shown in FIG. 1. The $IC_{50}$ of the particles of hydrophobised chitosan determined using FIG. 1 is equal to 0.04% w/v.

4.4. Activity of Antifungal Agents Against *Candida albicans*

4.4.1. Activity of Fungizone®

Protocol

Preparation of the Fungizone® solution: A flacon of injectable Fungizone® (50 mg) is reconstituted with 10 ml of water for injectable preparations. The suspension obtained contains 5 mg/ml of amphotericin B and deoxycholate in order to ensure the stability of the suspension. The minimum inhibitory concentration (MIC) observed on the reference strain of *Candida albicans* is 0.6 µg/ml in the conditions of the test. The MIC corresponds approximately to the $IC_{90}\%$.

The test is carried out in a 96-well dilution microplate (8 lines A-H, 12 columns). 200 µL of culture medium are added to the wells of the first column (1) and only 100 µL in the wells of the other columns (from 2 to 12).

The Fungizone® (10 µL), at a concentration of 0.1 mg/mL (it is diluted to 1/50), is added to the well of column 1. The cascade dilution technique of the wells of the column 1 is used in such a way as to have at each time a dilution at 1/2 by passing from one well to the other until the wells of the column 12 are reached.

200 µL of suspension of *Candida albicans* (inoculum) are added to each well. The concentration of Fungizone® in the wells of the column 1 is 2.5 µg/mL or 2.5 mg/L ($2.5 \times 10^{-4}\%$ m/v). The dilution microplate is incubated at 35° C. for 24 h.

The control consists in proceeding in the same way but without adding Fungizone®.

Figure 2:
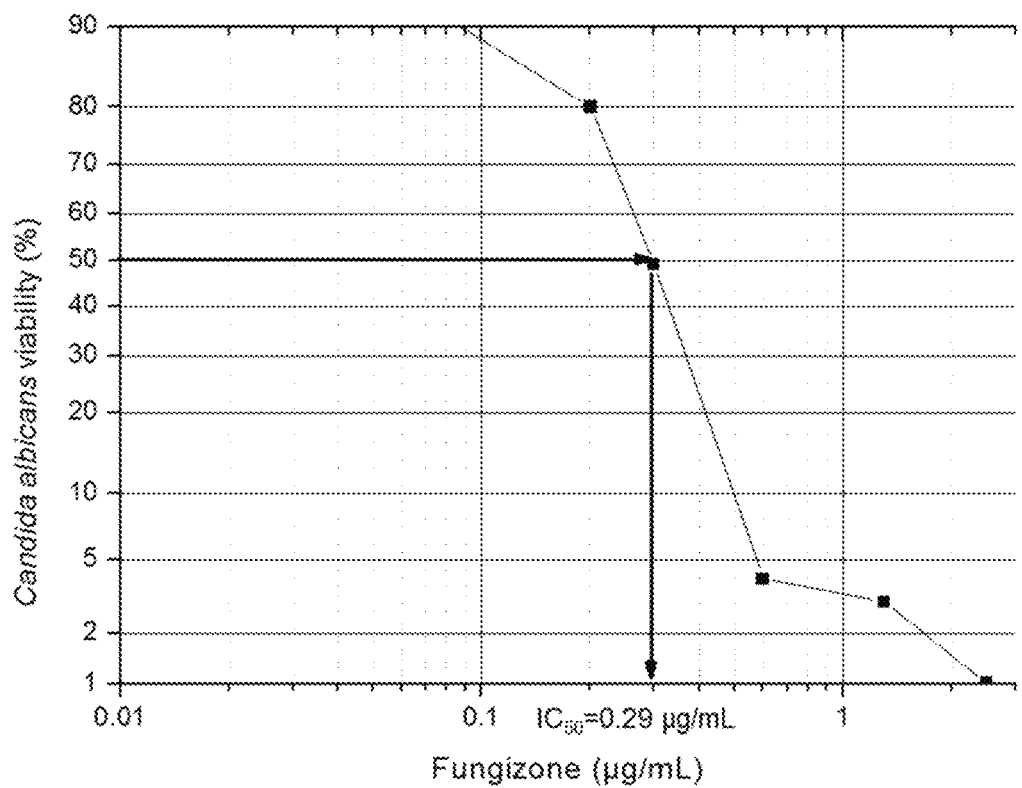
FIG. 2 is a graph representing the viability of *Candida albicans* in function to the concentration in Fungizone®, for the determination of the $IC_{50}$ of Fungizone® against *Candida albicans*.

The percentage of viability of *Candida albicans* is evaluated by using the test with MTT, as described hereinabove. The Test was Carried Out at Least Three Times Using Different Cultures on Agar of the Strain of *Candida albicans*. Results The results of the activity of the Fungizone® against *Candida albicans* are shown in FIG. 2. The $IC_{50}$ of Fungizone® determined using FIG. 2 is equal to 0.3 µg/mL.

4.4.2. Activity of Chlorhexidine Digluconate

Protocol

The test is carried out in a 96-well dilution microplate (8 lines A-H, 12 columns). 200 µL of culture medium are added to the wells of the first column (1) and only 100 µL in the wells of the other columns (from 2 to 12).

The chlorhexidine digluconate (10 µL) at a concentration of 5 mg/mL is added to the well of column 1. The cascade dilution technique of the wells of the column 1 is used in such a way as to have at each time a dilution at 1/2 by passing from one well to the other until the wells of the column 12 are reached.

100 µL of suspension of *Candida albicans* (inoculum) are added to each well. The concentration of chlorhexidine digluconate in the wells of the column 1 is 2.5 µg/mL ($2.5 \times 10^{-4}\%$ m/v). The dilution microplate is incubated at 35° C. for 24 h.

The control consists in proceeding in the same way but without adding chlorhexidine digluconate.

Figure 3:
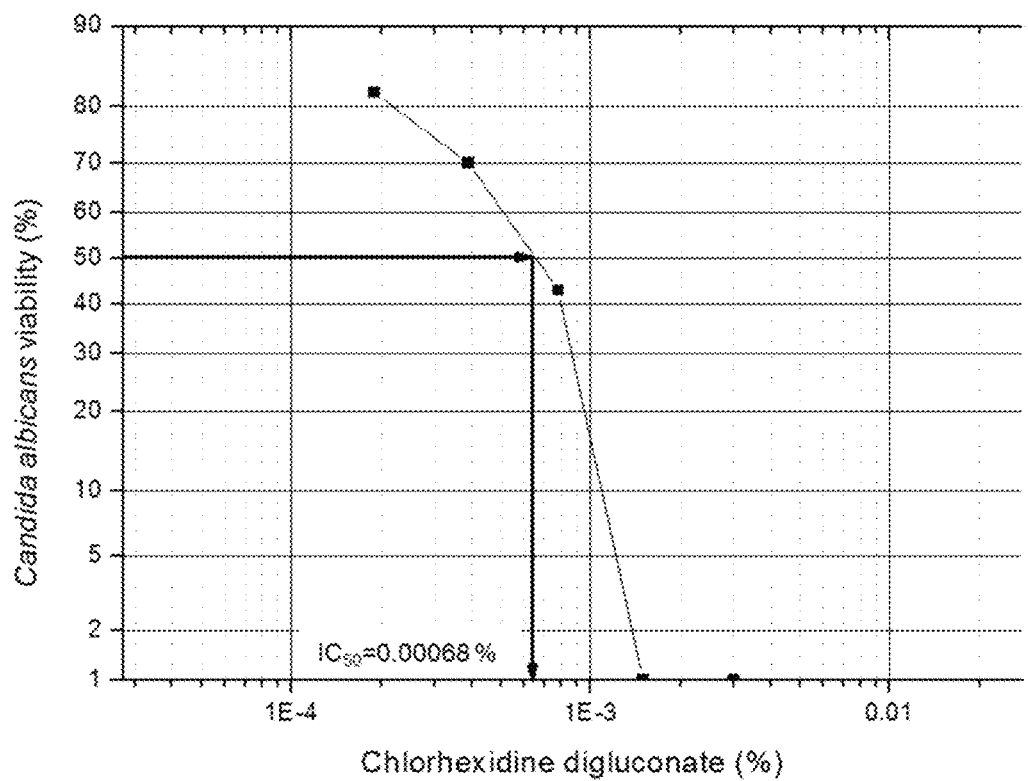
FIG. 3 is a graph representing the viability of *Candida albicans* in function to the concentration in chlorhexidine digluconate, for the determination of the $IC_{50}$ of chlorhexidine digluconate against *Candida albicans*.
Figure 4A:
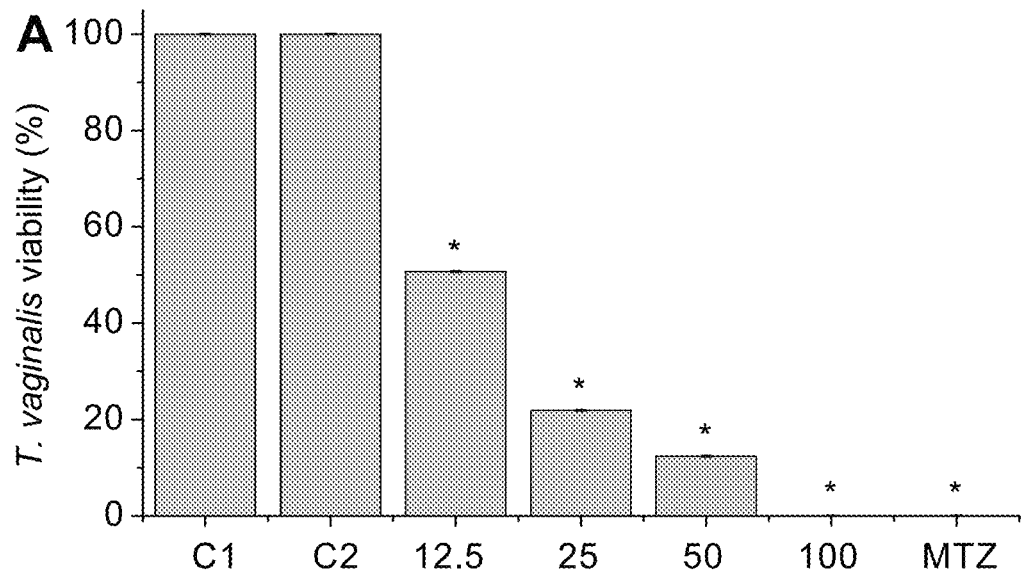
FIGS. 4A to 4D is a series of histograms showing the effect of the proportion of thiol in the nanoparticle on the viability of *Trichomonas vaginalis* after incubation of 24 h in the presence of nanoparticles; the compositions of the nanoparticles PIBCA-[chitosan20/chitosan20-TBA] are the following: PIBCA-[chitosan20/chitosan20-TBA] 100/0% m/m (FIG. 4A), 75/25% m/m (FIG. 4B), 50/50% m/m (FIG. 4C), 25/75% m/m (FIG. 4D), at different concentration in nanoparticles (12.5, 25, 50 and 100 μg/mL). The concentrations in nanoparticles tested are 12.5, 25, 50 and 100 μg/mL. The viability of *Trichomonas vaginalis* was measured in the culture medium without nanoparticles (C1) and in the polymerisation medium in nanoparticles (C2). MTZ was used as an anti *Trichomonas vaginalis* reference compound at a concentration of 7 μg/mL. The values are the average values of 3 measurements±sd; * percentage with respect to the control p<0.05.
Figure 4B:
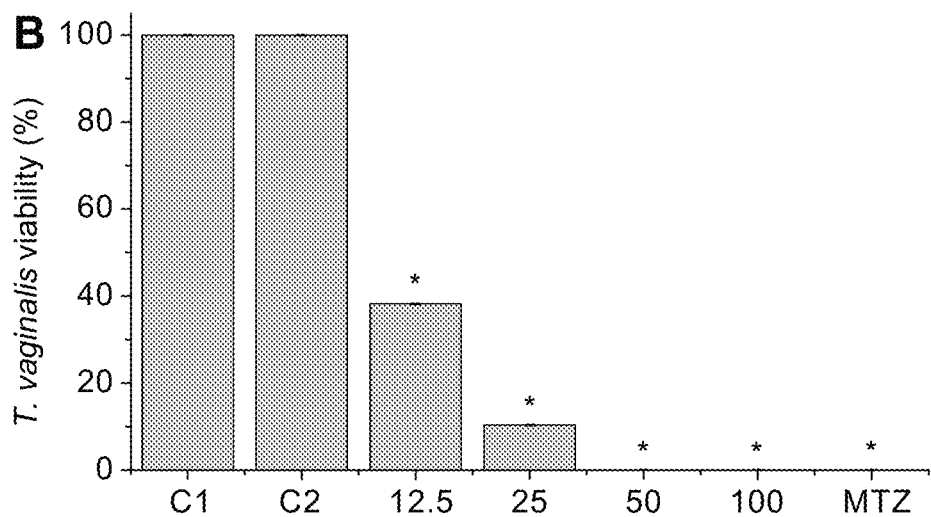
Figure 4C:
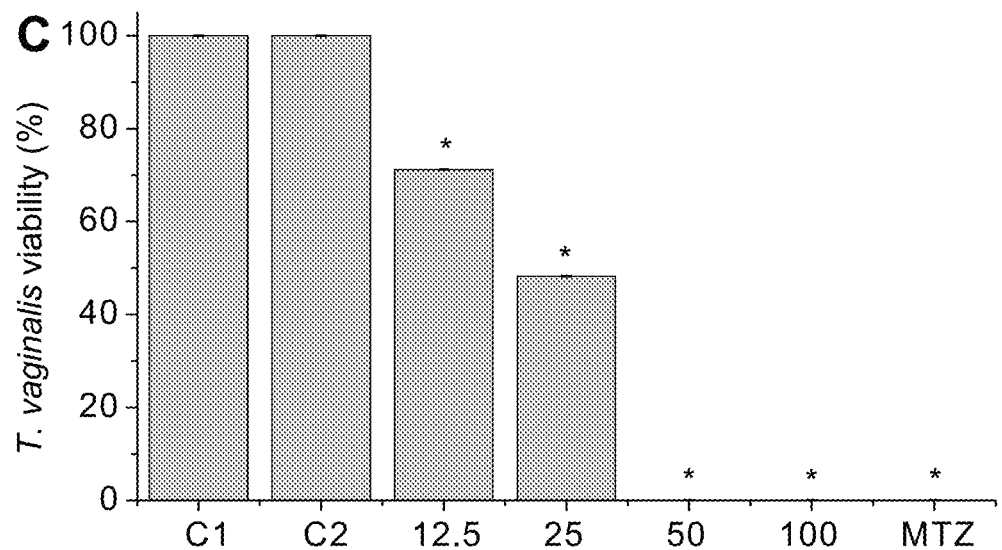
Figure 4D:
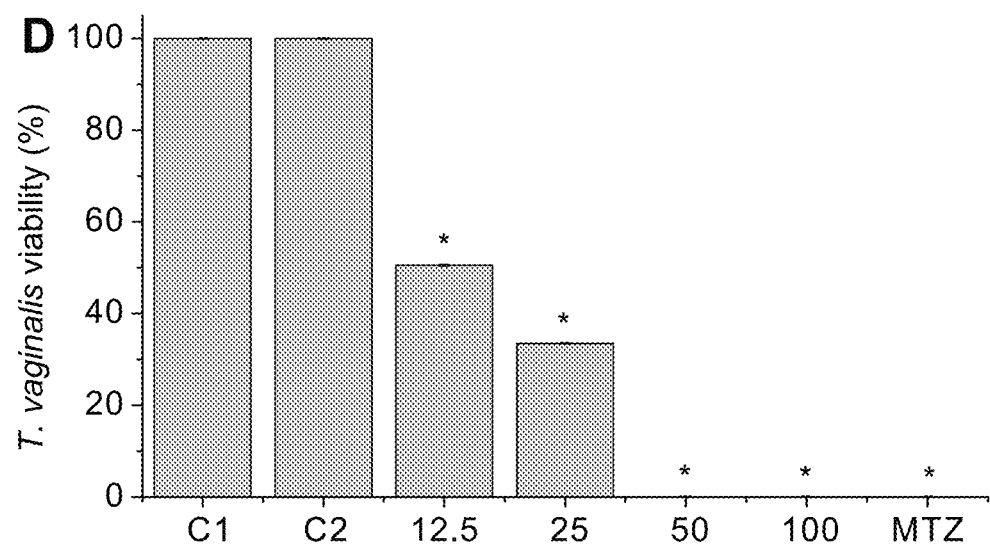

The percentage of viability of *Candida albicans* is evaluated by using the test with MTT, in the same conditions as previously.
Results The results of the activity of the chlorhexidine digluconate against *Candida albicans* are shown in FIG. 3. The $IC_{50}$ of the chlorhexidine digluconate determined using FIG. 3 is equal to 0.00068%.

4.5. Activity of the Compositions of the Invention Against *Candida albicans*

4.5.1. Composition 1: Fungizone® Associated with Particles of Hydrophobised Chitosan and of Cyclodextrin Protocol The test is carried out in a 96-well dilution microplate (8 lines A-H, 12 columns). 200 µL of buffer RPMI medium are added to the wells of the first column (1) and only 100 µL in the wells of the other columns (from 2 to 12).

The suspension of particles of hydrophobised chitosan (50 µL) (cf. part 4.3) as well as the Fungizone® (10 µL) at a concentration of 5 mg/mL are added to each well of the column 1. The cascade dilution technique of the particles of the wells of the column 1 is used in such a way as to have at each time a dilution at 1/2 by passing from one well to the other until the wells of the column 12 are reached.

200 µL of suspension of *Candida albicans* (inoculum) are added to each well. The concentration of the hydrophobised chitosan in the wells of the column 1 is 0.12%. The concentration of Fungizone® in the wells of the column 1 is 1.9 µg/mL (1.9×10$^{-4}$% m/v). The dilution microplate is incubated at 35° C. for 24 h.

The control consists in proceeding in the same way but without adding the suspension of particles of hydrophobised chitosan or the Fungizone®.

The percentage of viability of *Candida albicans* is evaluated by using the test with MTT, in the same conditions as previously.

The test was carried out at least three times using different cultures on agar of the strain of *Candida albicans*.

Results

Details on the results of the antifungal activity of the composition comprising the Fungizone® and of the particles of hydrophobised chitosan are provided hereinbelow. The effect of the association is determined by the method Odds, for which the details were provided hereinabove.

Step (1): $IC_{50}$ (µM) of Each Molecule Alone:
Molecule A: Fungizone® 0.5% p/v (5 mg/mL)
$IC_{50}^{A}$=0.3 10$^{-4}$% p/v (0.3 µg/mL)
Molecule B: Hydrophobised Chitosan Formulated in Microparticles
$IC_{50}^{B}$=0.04% p/v Steps (2) to (5): $IC_{50}$ of Each Association ($IC_{50}^{A}$ Assoc.1 and $IC_{50}^{B}$ Assoc.1):

$IC_{50}^{A}$ assoc.1 = 0.028 10$^{-4}$% (0.028 µg/mL)    $IC_{50}^{B}$ assoc.1 = 0.0009%
$IC_{50}^{A}$ assoc.2 = 0.023 10$^{-4}$% (0.023 µg/mL)    $IC_{50}^{B}$ assoc.2 = 0.0023%
$IC_{50}^{A}$ assoc.3 = 0.023 10$^{-4}$% (0.021 µg/mL)    $IC_{50}^{B}$ assoc.3 = 0.0041%
$IC_{50}^{A}$ assoc.4 = 0.023 10$^{-4}$% (0.022 µg/mL)    $IC_{50}^{B}$ assoc.4 = 0.0119%

Step (6): Fractional Inhibitory Concentrations (FIC):

| $FIC_A^1 = IC_{50}^{A(assoc.1)}/IC_{50}^{A}$ and $FIC_B^1 = IC_{50}^{B(assoc.1)}/IC_{50}^{B}$ | |
|---|---|
| $FIC_A^1$ = 0.093 | $FIC_B^1$ = 0.0225 |
| $FIC_A^2$ = 0.076 | $FIC_B^2$ = 0.0575 |
| $FIC_A^3$ = 0.070 | $FIC_B^3$ = 0.1025 |
| $FIC_A^4$ = 0.073 | $FIC_B^4$ = 0.2975 |

Step (7): Calculation of ΣFIC for Each Combination
$\Sigma FIC_1 = FIC_A^1 + FIC_B^1$
$\Sigma FIC_1$=0.1155
$\Sigma FIC_2$=0.1335
$\Sigma FIC_3$=0.1725
$\Sigma FIC_4$=0.3705

Step (8): Calculation of FICI=[$\Sigma FIC_1 + \Sigma FIC_2 + \Sigma FIC_3 + \Sigma FIC_4$]/4:

The result of the FICI=0.198 which clearly indicated a synergy between the Fungizone® and the particles of hydrophobised chitosan in the composition tested.

4.5.2. Composition 2: Chlorhexidine Digluconate Associated with Particles of Hydrophobised Chitosan and of Cyclodextrin Protocol The protocol is the same as the one used for the composition 1 hereinabove.

The chlorhexidine digluconate is added at a concentration of 1%.

The concentration of the hydrophobised chitosan in the wells of the column 1 is 0.12%. The concentration of the chlorhexidine digluconate in the wells of the column 1 is 0.025%.

Results

Details on the results of the antifungal activity of the composition comprising the chlorhexidine digluconate and of the particles of hydrophobised chitosan are provided hereinbelow. The effect of the association is determined by the Odds method, for which the details were provided hereinabove.

Step (1): $IC_{50}$ (µM) of Each Molecule Alone:
Molecule A: Chlorhexidine digluconate 1%
$IC_{50}^{A}$=0.00068%
Molecule B: Hydrophobised chitosan formulated in microparticles
$IC_{50}^{B}$=0.04%

Steps (2) to (5 $IC_{50}$ of Each Association ($IC_{50}^{A}$ Assoc.1 and $IC_{50}^{B}$ Assoc.1):

$IC_{50}^{A}$ assoc.1 = 0.000295%    $IC_{50}^{B}$ assoc.1 = 0.0047%
$IC_{50}^{A}$ assoc.2 = 0.000235%    $IC_{50}^{B}$ assoc.2 = 0.0095%
$IC_{50}^{A}$ assoc.3 = 0.000155%    $IC_{50}^{B}$ assoc.3 = 0.0015%
$IC_{50}^{A}$ assoc.4 = 0.000170%    $IC_{50}^{B}$ assoc.4 = 0.041%

Step (6): Fractional Inhibitory Concentrations (FIC):

| $FIC_A^1 = IC_{50}^{A(assoc.1)}/IC_{50}^{A}$ and $FIC_B^1 = IC_{50}^{B(assoc.1)}/IC_{50}^{B}$ | |
|---|---|
| $FIC_A^1$ = 0.434 | $FIC_B^1$ = 0.1175 |
| $FIC_A^2$ = 0.346 | $FIC_B^2$ = 0.2375 |
| $FIC_A^3$ = 0.228 | $FIC_B^3$ = 0.375 |
| $FIC_A^4$ = 0.25 | $FIC_B^4$ = 1.025 |

Step (7): Calculation of ΣFIC for Each Combination
$\Sigma FIC_1 = FIC_A^1 + FIC_B^1$:
$\Sigma FIC_1$=0.5515
$\Sigma FIC_2$=0.5835
$\Sigma FIC_3$=0.603
$\Sigma FIC_4$=1.275

Step (8): Calculation of FICI=[$\Sigma FIC_1 + \Sigma FIC_2 + \Sigma FIC_3 + \Sigma FIC_4$]/4:

The result of the FICI=0.753 which clearly indicates an additive effect between the chlorhexidine and the particles of hydrophobised chitosan in the composition tested.

5. Antiparasitic Activities of the Compositions of the Invention 5.1. Antiparasitic Activity Against *Leishmania*

The antiparasitic activity of the compositions of the invention were studied on strains of *Leishmania*:

The compositions 5a (PIBCA-[chitosan20/chitosan20-TBA] 100/0 m/m %) and 4 (MC3+α-cyclodextrin 1/10% m/v), described in point 3 hereinabove, have been tested in vitro on three strains of *Leishmania*: *Leishmania major* (MHOM/SU/73/5-ASKH/LEM134), *Leishmania tropica* (LRC-L39/LEM2563), *Leishmania braziliensis* (MHOM/BR/75/M2903b). The $IC_{50}$ were measured then compared to the reference product amphotericin B in order to determine the anti-leishmanial activity of the nanoparticles.

Material

The promastigote culture was carried out at 26° C. in M199 medium (Sigma, Saint-Quentin Fallavier, France) supplemented with 4.2 mM $NaHCO_3$, 10% of foetal calf serum inactivated by heat (Invitrogen, Saint-Aubin, France), 40 mM Hepes pH 7.5, 100 µM adenosine and 20 µM haemin (complete M199 medium).

The culture of the axenic amastigotes was carried out at 37° C. in a complete M199 medium supplemented with 200 µM $CaCl_2$ and 200 µM $MgCl_2$.

The macrophages RAW 264.7 were maintained at 37° C. with 5% $CO_2$ in DMEM medium (Dulbecco's modified Eagle's medium, Gibco, Saint-Aubin, France) supplemented with 10% of foetal calf serum, inactivated by heat (Invitrogen, Saint-Aubin, France), also called complete DMEM medium.

Methods

In Vitro Evaluation on Promastigotes

The test of the compositions on prosmatigotes was conducted as previously described (Saint-Pierre-Chazalet et al., J. Antimicrob. Chemother., 2009, 64, 993-1001). Series of dilutions were carried out in 100 µl of complete M199 medium in a 96-well plate. Promastigotes in exponential growth were then added to each well at a rate of $10^6$/ml in a final volume of 200 µl. After 72 h of incubation at 26° C., the viability of the promastigotes was measured by using 250 µg/ml of MTT, or 3-(4,5-dimethylthiazol-2-yl)-2,5-diphenyl tetrazolium bromide (Sigma, Saint-Quentin Fallavier, France), which is reduced in formazan, an insoluble product, by the active mitochondria of the living cells. After 4 h of incubation at 26° C., the formazan is then solubilised by adding 100 µl of isopropanol containing 40 mM of HCl in each well, then incubating for 15 minutes under stirring. The viability of the cells was then quantified by measuring the absorbance at 570 nm using a plate reader (Labsystems Multiskan MS). The activity of the compositions is expressed in $IC_{50}$. Amphotericin B is used as a reference product.

In Vitro Evaluation on Axenic Amastigotes

Axenic amastigotes were induced by incubating promastigotes in complete M199 medium supplemented with 200 µM of $CaCl_2$ and 200 µM $MgCl_2$ at 37° C. with 5% $CO_2$ for 48 h. Serial two-fold dilutions of the compositions were then carried out in 100 µl of the same medium in 96-well plates. The axenic amastigotes were then added in each well at $10^6$/ml in 200 µl of final. volume After 72 h of incubation at 37° C. with 5% $CO_2$, 20 µl of resazurin at 450 µM were added in each well, then incubated in the dark for 24 h at 37° C. with 5% $CO_2$. In living cells, resazurin is reduced in resofurin. This conversion is monitored by measuring the absorbance at specific wavelengths of the resofurin (570 nm) and of the resazurin (600 nm) by using a microplate reader (Labsystem Multisken MS). The activity of the compositions is expressed in $IC_{50}$. Amphotericin B is used as a reference product.

In Vitro Evaluation on Intramacrophagic Amastigotes

The evaluation of the compositions 5a and 4 on intramacrophagic amastigotes was conducted as previously described (Audisio et al., Eur. J. Med. Chem., 2012, 52, 44-50). The macrophages RAW 264.7 were added in the wells of 96-well plates at a rate of $2\times10^4$ cells per well and incubated for 24 h at 37° C. with 5% $CO_2$. The axenic amastigotes were then induced as described hereinabove, centrifuged at 2000 g for 10 minutes, then resuspended in a complete DMEM medium, and added to each well at a rate of $3.2\times10^5$ parasites per well, in order to reach a parasite/macrophage ratio of 16:1. After 24 h of infection at 37° C. with 5% $CO_2$, the extracellular parasites were removed and 100 µl of complete DMEM medium containing the seried dilutions of the compositions were added to each well. After 48 h of treatment, the culture medium is removed, then replaced with 100 µl of DirectPCR Lysis reagent (Euromedex, Souffelweyersheim, France), and three freezing-thawing cycles at ambient temperature are then carried out, then 50 µg/ml of proteinase K are added, and a final incubation at 55° C. for 4 hours is carried out in order to allow for the complete lysis of the cells. 10 µl of each extract were then added to 40 µl of DirectPCR Lysis reagent containing 0.05% Sybr Green I (Invitrogen, Saint-Aubin, France). The fluorescence of the DNA was measured using the Mastercycler® realplex (Eppendorf, Montesson, France). The activity of the compositions is expressed in the form of $IC_{50}$. Amphotericin B is used as a reference product.

Results

The results of the in vitro tests carried out on the three strains of *Leishmania* with the composition 5a and the composition 4 are presented in the table hereinbelow. The results with amphotericin B are also presented as a reference.

|  |  | Composition | | |
| --- | --- | --- | --- | --- |
|  |  | Composition 5a $IC50$ (ng/µl) ± SEM | Composition 4 $IC50$ (ng/µl) ± SEM | Amphotericin B-DOC IC50 (ng/µl) ± SEM |
| *Leishmania major* | promastigotes | 0.051 ± 0.001 | 43.09 ± 6.97 | 0.015 ± 0.004 |
|  | axenic amastigotes | 0.043 ± 0.01 | 11.99 ± 2.88 | 0.038 ± 0.002 |
|  | intramacrophagic amastigotes | 5.93 ± 0.43 | 21.86 ± 6.66 | 0.49 ± 0.13 |
| *Leishmania braziliensis* | promastigotes | 0.127 ± 0.007 | 36.38 ± 5.15 | 0.022 ± 0.005 |
|  | axenic amastigotes | 0.9 ± 0.31 | 25.32 ± 13.09 | 0.055 ± 0.014 |
|  | intramacrophagic amastigotes | 7.49 ± 0.19 | 33.29 ± 12.98 | 0.29 ± 0.09 |
| *Leishmania tropica* | promastigotes | 0.174 ± 0.034 | 87.06 ± 0.69 | 0.023 ± 0.002 |
|  | axenic amastigotes | 0.142 ± 0.015 | 32.3 ± 10.86 | 0.049 ± 0.01 |
|  | intramacrophagic amastigotes | 3.96 ± 0.74 | 12.05 ± 4 | 0.51 ± 0.07 |

Interpretation

The compositions of the invention tested on the different strains of *Leishmania* have interesting antiparasitic activities, in particular composition 5a which has $IC_{50}$ less than 10 ng/µl, comparable to the reference product, and this, regardless of the strain of *Leishmania*.

5.2. Antiparasitic Activity Against *Trichomonas vaginalis*

The antiparasitic activity of the compositions of the invention were studied against *Trichomonas vaginalis*:

5.2.1. Material

The Pluronic® F127 (Poloxamer P407) and Pluronic® F68 (Poloxamer 188) pharmaceutical quality copolymers come from BASF ChemTrade GmbH (Ludwigshafen, Germany). MTZ, the phosphate buffer solution (PBS, 0.01 M, pH 7.4 at 25° C.) and all of the other reagents used for the preparation of simulated vaginal fluid (simulated vaginal fluid (SVF)) and for the thiolation of the chitosan come from Sigma-Aldrich (Saint-Quentin Fallavier, France). The isobutylcyanoacrylate (IBCA) was offered by Henkel Biomedical (Dublin, Ireland). The Traut (2-iminothiolane) reagent was synthesised in the organic chemistry department (Biocis UMR CNRS 8076), School of Pharmacy, University Paris-Sud (Chatenay-Malabry, France). The strain *Trichomonas vaginalis* (ATCC PRA-98; Taxonoly ID: 412133) was stored in liquid nitrogen containing 6% dimethyl sulfoxide as a cryoprotector. This strain was sensitive to MTZ.

The simulated vaginal fluid (SVF) was prepared as previously described by Owen and Katz (Owen and Katz, Contraception, 1999, 59, 91-95): NaCl (3.51 g), KOH (1.4 g), Ca(OH)$_2$ (0.22 g), bovine serum albumin (0.018 g), lactic acid (2.00 g), acetic acid (1.00 g), glycerol (0.16 g), urea (0.4 g) and glucose (5.00 g) are added to 900 mL of distilled water contained in a beaker and mechanically stirred until dissolution is complete. The pH of the mixture is then adjusted to 4.5 by adding HCl. The pH is fixed at 4.5, which corresponds to the normal value range of pre-menopause vaginal pH. The final volume was adjusted to 1 L.

The chitosan hydrosoluble comes from Amicogen (Seoul, Korea). The average molecular weight is 20,000 g/mol according to the manufacturer. This chitosan is called "chitosan20" hereinafter. The degree of deacetylation is 92%. The insertion of the thiol groups on the chitosan was carried out according to the method developed by Bernkop-Schntirch et al., such as described in point 1.3 hereinabove. The dialysed products are frozen (Christ Alpha 1-4 freeze-dryer. Bioblock Scientific, Illkirch, France) then stored at −20° C. until they are used. The final polymer is chitosan-4-thiol-butylamidine, referred to hereinafter as "chitosan20-TBA".

5.2.2. Method
Preparation of PIBCA-Chitosan Nanoparticles

The PIBCA-chitosan and thiolated PIBCA-chitosan nanoparticles were prepared via emulsion anionic polymerisation according to the method described by Bravo-Osuna et al., such as detailed hereinabove in point 1.4.2. The compositions 5a to 5d such as presented hereinabove have been tested.

Particles of PIBCA, without chitosan or thiolated chitosan, were prepared in the same way by replacing the chitosan and the thiolated chitosan with Pluronic® F68 for 1% m/v acting as a stabiliser. In what follows, these particles are referred to as "PIBCA/F68 nanoparticles".

The suspensions of nanoparticles were purified by dialysis by using a Spectra/Por® membrane with a molecular weight selection of 100,000 g/mol, for two cycles of 30 minutes, then a cycle of 60 minutes and an overnight cycle with 1 liter of solution of acetic acid at 16 µM. The suspensions of nanoparticles are stored at 4° C. until used.

The polymerisation medium, used as a control medium (control 2, noted as C2) for the evaluation of the anti-*Trichomonas vaginalis* activity, was prepared in the way as described hereinabove, but without IBCA, or chitosan or Pluronic® F68, then purified in the same conditions as for the purification of nanoparticles.

Physical-Chemical Characterisations of the Nanoparticles

The average hydrodynamic diameter of the nanoparticles and their size distribution were determined by the average Z obtained at 20° C. by quasi-elastic light scattering with a Zetasizer Nanoseries (Malvern Instruments Ltd. UK). The angle of dispersion was set to 173° and 60 µL of each sample was diluted in 2 mL of a solution of acetic acid at 0.16 µM (Millex, SLAP 0225, Millipore, France). The Zeta potential of the nanoparticles was measured with Zetasizer Nanoseries (Malvern Instruments Ltd. UK). The dilution of the suspensions (1:33 (v/v)) was conducted with a solution of NaCl (1 mM). Each experience was carried out in 3 copies.

Preparation of the Hydrogels

Hydrogels were prepared as described above (Bouchemal K. et al., Aka-Any-Grah A. et al., Zhang M. et al.): hydrogels of Pluronic® F127 (20 m/m %) were obtained by progressively adding under stirring the Pluronic® F127 as a powder into water maintained at 4° C. The hydrogel containing the nanoparticles was prepared by slowly scattering under magnetic stirring the Pluronic® F127 in powder (20 m/m %) directly into the dispersion of nanoparticle maintained at 4° C. until the polymer is completely dissolved. The nanoparticles are comprised of PIBCA-[chitosan20/chitosan20-TBA] 75/25 m/m % (composition 5a to 5d). The concentration in nanoparticles in the hydrogel is 20 mg/mL.

Evaluation of the Anti *Trichomonas vaginalis* Activity of the Compositions

*Trichomonas vaginalis* is axenically cultivated at 35° C. in a trypticase-yeast extract-maltose medium (TYM) (Diamond L. S. et al., J. Parasitol., 1957, 43(4), 488-490) enriched with 10% of decomplemented horse serum (Gibco, France); the strain is subcultured every other day (Camuzat-Dedenis B. et al., Eur. J. Med. Chem., 2001, 36(10), 837-842).

The tubes of culture containing the fresh TYM medium enriched with 10% of horse serum alone (control 1, noted as C1) or those with the compositions tested, are inoculated with the parasite at a rate of $2 \times 10^5$ protozoa in 3 mL. The compositions tested are the compositions of PIBCA-[chitosan20/chitosan20-TBA] that have different proportions of chitosan and of thiolated chitosan, namely 100/0, 75/25, 50/50 and 25/75 m/m %. The concentrations in nanoparticles studied are 12.5, 25, 50 and 100 µg/mL.

The results are compared between (i) the nanoparticles of PIBCA/F68; (ii) the solutions comprised of mixtures of PIBCA-[chitosan20/chitosan20-TBA] having different proportions of chitosan and thiolated chitosan, namely 100/0, 75/25, 50/50 and 25/75 m/m %, (iii) the polymerisation medium (control 2, noted as C2). MTZ is used as an anti *Trichomonas vaginalis* reference product at a lethal concentration of 7 µg/mL.

The tubes are incubated for 24 h at 35° C. and the number of parasites per milliliter in each tube is determined microscopically with a haemocytometer (Kova® Glasstic® Slide 10, Hycor Biomedical, United States). The experiments are repeated three times.

The results are expressed in the form of a percentage of inhibition of the cell culture according to control 1.

For the statistical analysis, the Student test was applied. The significance threshold is $p<0.05$.

Ex Vivo Evaluation of Toxicity of the Compositions on the Vaginal Mucous of Pig

The experiments were conducted on female pigs ((INRA Jouy en Josas, France) weighing between 60 and 63 kg on the average. The animals fasted for 24 hours but have free access to running water. All of the experiments on the animals were compliant with European Directive (ED/86/609/EEC) and were conducted in compliance with authorisation No. 78-16 from the French ministry of agriculture. The pigs are sacrificed by intravenous injection (20 mL) of an overdose of sodium phenobarbital (Dolethal, Vetoquinol Laboratory, Lure, France) and the vaginal mucosa is sampled over a length of 10 cm. The mucous is then placed in the simulated vaginal fluid (SVF) and placed at −20° C. immediately after the sacrifice of the animal then stored at this temperature until the next use. It has been shown that pig mucosa could be frozen in order to store them without the mucous layer being affected (Squier C A. et al.). The samples are cut into pieces of 1 cm² using surgical scissors in order to obtain intact vaginal tissues then thawed before the experiment at ambient temperature in freshly prepared SVF.

The mucous is then placed in the Franz cells and the collection compartment is filled with SVF (11.2 mL). About 0.5 mL of each composition is evenly deposited on the mucous. The contact surface is 1 cm². The composition studied is comprised of gelled PIBCA-[chitosan20/chitosan20-TBA] 75/25 m/m % with Pluronic® F127. The controls are: the SVF, Pluronic® F127 and the nanoparticles without hydrogel. The concentration in nanoparticles is 20 mg/mL and the concentration in Pluronic® F127 is 20 m/m %.

The Franz cells are closed and placed in a thermostatically-controlled water bath at 37° C. After 12 hours in contact with the compositions, the acceptor and donor liquids are collected. The tissues are fixed in FineFix (Milestone, Italy), incorporated into paraffin and cut into thin 4 μm slices. The coloration with hematoxilin-eosin-saffranin was done before the histological analyses. The images were obtained with an Axiophot Zeiss microscope (Germany) connected with a digital camera (PCO, Germany). All of the samples were scanned with a slide scanner (Nikon Super Coolscan 8000) suited to the histopathology (Regional Group on Cancer Studies, Caen, France).

5.2.3. Results

Physical-Chemical Characterisations of the Nanoparticles

The nanoparticles of PIBCA-[chitosan20/chitosan20-TBA] were obtained by emulsion anionic polymerisation by polymerisation of the monomer of isobutylcyanoacrylate. These nanoparticles are composed of a hydrophobic core of PIBCA while the outer shell is formed by a layer of a mixture of chitosan and of thiolated chitosan with different proportions in thiol 100/0, 75/25, 50/50 and 25/75 m/m %. The nanoparticles without chitosan are stabilised with Pluronic® F68. The average hydrodynamic diameters of the nanoparticles vary between 185 and 210 nm:

| Composition of the nanoparticles (% m/m) | | $D_h$ (nm) | ζ Potential (mV) |
|---|---|---|---|
| PIBCA-[chitosan20/chitosan20-TBA] | 100/0 | 185 ± 2 | +39.6 ± 0.6 |
| | 75/25 | 211 ± 4 | +34.3 ± 1.0 |
| | 50/50 | 196 ± 2 | +39.0 ± 0.4 |
| | 25/75 | 192 ± 2 | +40.4 ± 0.8 |

The electrophoretic mobility measurements showing that the zeta potentials of the nanoparticles PIBCA-chitosan are positive and vary between +34.3 to +40.4 mV. These values differ slightly according to the composition of the shell of the nanoparticle.

In Vitro Evaluation of the Anti-*Trichomonas vaginalis* Activity of the Compositions The anti-*Trichomonas vaginalis* activity of the nanoparticles comprised of PIBCA-[chitosan20/chitosan20-TBA] 75/25 m/m % was studied after incubation of 24 hours with *Trichomonas vaginalis*. The anti *Trichomonas vaginalis* activity of the nanoparticles is compared with the activity of the reference molecule, MTZ, used at a lethal concentration of 7 μg/mL.

The nanoparticles tested show a powerful anti-*Trichomonas vaginalis* effect at a concentration of 100 μg/mL (FIGS. 4A-4D). The variation of the proportion in thiolated chitosan does not affect the anti-*Trichomonas vaginalis* activity. Indeed, a similar anti-*Trichomonas vaginalis* activity was observed with the compositions having different ratios (PIBCA-[chitosan20/chitosan20-TBA] 100/0, 75/25, 50/50 and 25/75 m/m %) (FIG. 4A to 4D).

Figure 5:
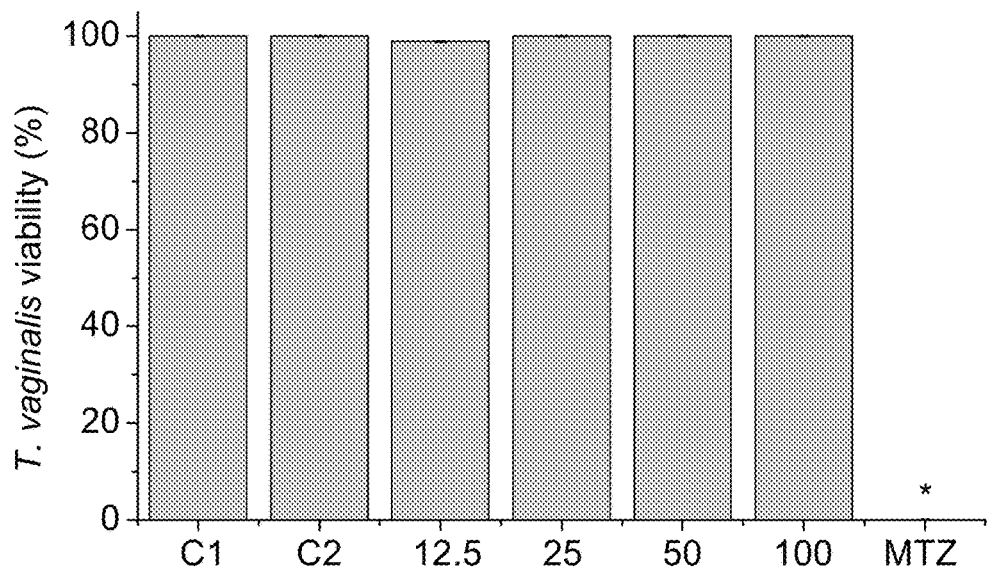
FIG. 5 is a histogram representing the effect of nanoparticles of PIBCA-F68 at different concentrations on the viability of *Trichomonas vaginalis*. The concentrations in nanoparticles tested are 12.5, 25, 50 and 100 μg/mL. The viability of *Trichomonas vaginalis* was measured in the culture medium without nanoparticles (C1) and in the polymerisation medium without nanoparticles (C2). MTZ was used as an anti *Trichomonas vaginalis* reference compound at a concentration of 7 μg/mL. The values are the average values of 3 measurements±sd; * percentage with respect to the control p<0.05.
Figure 6:
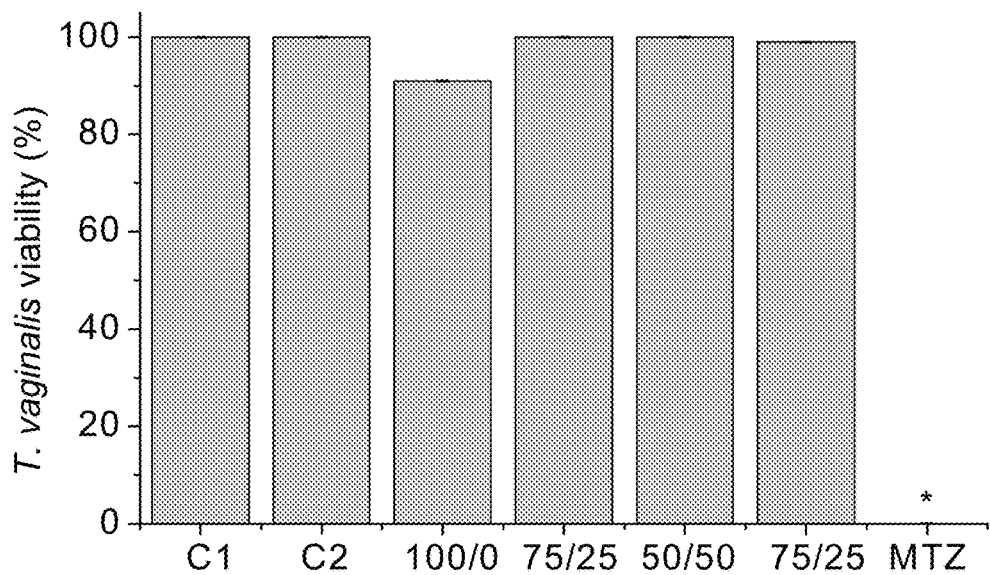
FIG. 6 is a histogram representing the effect of the proportion of thiolated chitosan in solutions comprised of [chitosan20/chitosan20-TBA] 100/0, 75/25, 50/50 and 25/75 m/m % in solution, on the viability of *Trichomonas vaginalis*. The solutions have been tested at a concentration of 12.5 µg/mL in [chitosan20/chitosan20-TBA]. Identical results were obtained with concentrations of 25 µg/mL, 50 µg/mL and 100 µg/mL. The viability of *Trichomonas vaginalis* was measured in the culture medium without nanoparticles (C1) and in the polymerisation medium without nanoparticles (C2). MTZ was used as an anti *Trichomonas vaginalis* reference compound at a concentration of 7 µg/mL. The values are the average values of 3 measurements±sd; * percentage with respect to the control p<0.05.

No anti-*Trichomonas vaginalis* activity was observed on the nanoparticles of PIBCA/F68 (i.e. without chitosan) (FIG. 5), or with solutions of chitosan (i.e. without PIBCA) (FIG. 6). In addition, no activity was observed with the polymerisation medium (FIGS. 5 and 6).

Figure 7:
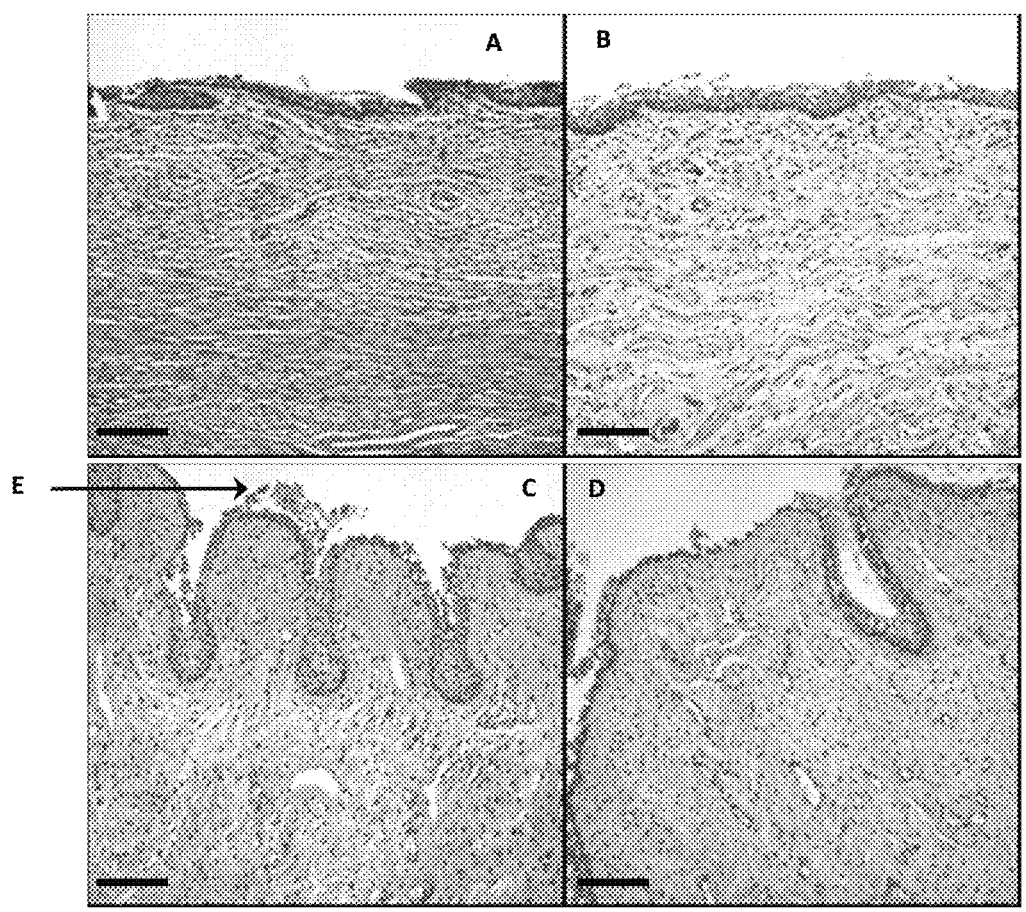
FIG. 7 is a series of histology images of vaginal mucous of pig after 12 h of contact with the (A) nanoparticles comprised of PIBCA/[Chitosan20/Chitosan20-TBA] 75/25% m/m gelled with F127 20% m/m, (B) SVF, (C) F127 20% m/m and (D) non-gelled PIBCA/[Chitosan20/Chitosan20-TBA] 75/25% m/m particles. The concentration in nanoparticles is 20 mg/mL. The scale bar corresponds to 0.02 cm. (Original Magnification×100). (E) mild focal desquamation without defective stroma.

Ex Vivo Evaluation of the Toxicity of the Compositions on the Vaginal Mucous of Pigs The histotoxicity of the gelled nanoparticles PIBCA-[chitosan20/chitosan20-TBA] 75/25 m/m % with Pluronic® F127 20 m/m % was studied ex vivo on vaginal mucous of pig. The results of FIG. 7A show that the epithelium was normal with a completely retained architecture in comparison with the experiment conducted in SVF (FIG. 7B) and Pluronic® F127 20 m/m % (FIG. 7C). In the presence of non-gelled particles, the epithelium has a normal architecture with a mild focal desquamation without stroma anomalies (FIG. 7D). The ulcerations are absent from all of the samples of mucosa and the base stroma is devoid of inflammatory cells which confirms the absence of a significant toxicity.

The invention claimed is:

1. A composition, comprising:
   (i) at least one antifungal agent mixed with a non-covalent inclusion complex formed by
   (ii) hydrophobised chitosan with the general formula (I):

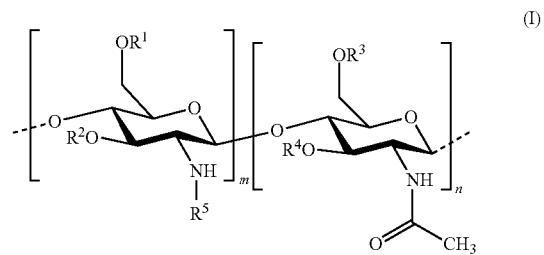

wherein
   $R^1$, $R^2$, $R^3$, $R^4$ and $R^5$ are identical or different, and each represents a moiety selected from the group consisting of:
      a hydrogen atom;
      a hydrophobic group; and
      a group substituted by a thiol function;
   provided that at least one of $R^1$, $R^2$, $R^3$, $R^4$ and $R^5$ is a hydrophobic group;
   n and m each independently represent an integer between 1 and 3000, provided that the percentage of m with respect to m+n is greater than 50%; and
   (iii) an α-cyclodextrin, said α-cyclodextrin being in the form of a monomer, wherein the antifungal agent is not encapsulated by the non-covalent inclusion complex.

2. The composition according to claim 1, wherein the hydrophobic group is selected from the group consisting of:
   a group with the formula —COR⁶, wherein R⁶ represents:
      a linear or branched alkyl group, comprising from 1 to 1000 carbon atoms;

a linear or branched alkenyl group, comprising from 2 to 1000 carbon atoms, and comprising at least one double bond C=C; and a poly(alkylcyanoacrylate) wherein the alkyl is linear or branched, comprising from 1 to 12 carbon atoms.

3. The composition according to claim 1, wherein the group substituted by a thiol function is an alkyl substituted by a thiol function, an alkenyl substituted by a thiol function, or a group —C(=NH$_2^+$X$^-$)—(CH$_2$)$_q$—SH, wherein X represents a halogen, and q represents an integer ranging from 1 to 10.

4. The composition according to claim 1, wherein the α-cyclodextrin is with the general formula (II):

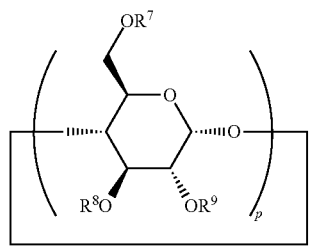

(II)

wherein
p is equal to 6, and
R$^7$, R$^8$ and R$^9$ are identical or different, and each independently represents a hydrogen atom or an alkyl group comprising 1 to 4 carbon atoms.

5. The composition according to claim 1, wherein the antifungal agent is selected from the group consisting of:
polyenes, amphotericin B, candicidin, filipin, hamycin, natamycin, nystatin, rimocidine;
imidazole compounds, bifonazole, butoconazole, clotrimazole, econazole, fenticonazole, isoconazole, ketoconazole, miconazole, omoconazole, oxiconazole, sertaconazole, sulconazole, tioconazole;
triazole compounds, albaconazole, fluconazole, isavuconazole, itraconazole, posaconazole, ravuconazole, terconazole, voriconazole;
triazole compounds, abafungine;
allylamines, amorolfine, butenafine, naftifine, terbinafine;
echinocandins, anidulafungine, caspofungine, micafungine;
benzoic acid, cerulenin, ciclopirox, olamine, flucytosine, 5-fluorocytosine, griseofulvine, haloprogine, polygodial, tolnaftate, undecylenic acid, crystal violet;
chlorhexidine, polyvinylpyrrolidone (PVP) iodine, benzalkonium chloride, and chlorine.

6. A pharmaceutical, dermatological, dermo-cosmestic or veterinary composition comprising the composition according to claim 1, in association with a pharmaceutically, dermatologically, dermo-cosmetically or veterinarily acceptable excipient.

7. The composition according to claim 6, wherein the composition is formulated to be administrable by at least one of parenteral, intramuscular, subcutaneous, intramedullary or intravenous route; by intrathecal injection, intraventricular, intraperitoneal or intraocular route; by oral, sublingual, nasal, aerosol, pulmonary, ear route; by topical, cutaneous, transdermal, ocular, rectal, vaginal route; by application on the nails; or by any other route that allows for a localised administration.

8. The composition according to claim 6, wherein the composition is in the form of a tablet, coated tablet, gastroresistant tablet, tablet, soft capsule, hard capsule, hard-shelled capsule; powder, pill, granule, solution, emulsion, suspension, syrup, eye drops, subgingival irrigation, mouth bath, chewing gum, toothpaste, patch, implant, suppository, paste, cream, gel, lotion, milk, ointment, spray, shampoo, varnish, plaster, catheter, compress, or gauze.

9. A medicament comprising the composition according to claim 1.

10. The composition according to claim 1, formulated for use as an antifungal agent or in the treatment of fungal infections.

11. A method for preparing the composition of claim 1, comprising the following steps:
(a) placing a hydrophobised chitosan with the general formula (I) in a solvent, in the presence of an α-cyclodextrin, under stirring, in order to form a suspension of particles; and
(b) adding at least one antifungal to the suspension.

12. A method for preparing the composition of claim 1, comprising the following steps:
(a) dissolving at least one antifungal agent in a solvent to form a solution;
(b) adding a hydrophobised chitosan with the general formula (I), and an α-cyclodextrin, to the solution formed in step (a); and
(c) stirring the mixture formed in step (b) to form a suspension of particles of chitosan and of cyclodextrin, encapsulating the at least one antifungal agent.

13. The composition according to claim 2, wherein the group substituted by a thiol function is an alkyl substituted by a thiol function, an alkenyl substituted by a thiol function, or a group —C(=NH$_2^+$X$^-$)—(CH$_2$)$_q$—SH, wherein X represents a halogen, and q represents an integer in a range of from 1 to 10.

14. The composition according to claim 2, wherein the α-cyclodextrin is with the general formula (II):

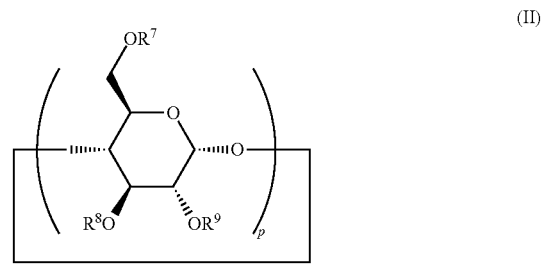

(II)

wherein
p is equal to 6, and
R$^7$, R$^8$ and R$^9$ are identical or different, and each independently represents a hydrogen atom or an alkyl group comprising 1 to 4 carbon atoms.

15. The composition according to claim 3, wherein the α-cyclodextrin is with the general formula (II):

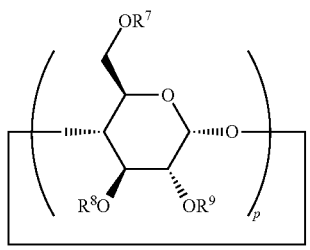 (II)

wherein
p is equal to 6, and
R$^7$, R$^8$ and R$^9$ are identical or different, and each independently represents a hydrogen atom or an alkyl group comprising 1 to 4 carbon atoms.

16. The composition according to claim 2, wherein the antifungal agent is selected from the group consisting of:
polyenes, amphotericin B, candicidin, filipin, hamycin, natamycin, nystatin, rimocidine;
imidazole compounds bifonazole, butoconazole, clotrimazole, econazole, fenticonazole, isoconazole, ketoconazole, miconazole, omoconazole, oxiconazole, sertaconazole, sulconazole, tioconazole;
triazole compounds, albaconazole, fluconazole, isavuconazole, itraconazole, posaconazole, ravuconazole, terconazole, voriconazole;
triazole compounds, abafungine;
allylamines, amorolfine, butenafine, naftifine, terbinafine;
echinocandins, anidulafungine, caspofungine, micafungine;
benzoic acid, cerulenin, ciclopirox, olamine, flucytosine, 5-fluorocytosine, griseofulvine, haloprogine, polygodial, tolnaftate, undecylenic acid, crystal violet;
chlorhexidine, polyvinylpyrrolidone (PVP) iodine, benzalkonium chloride, and chlorine.

17. The composition according to claim 3, wherein the antifungal agent is selected from the group consisting of:
polyenes, amphotericin B, candicidin, filipin, hamycin, natamycin, nystatin, rimocidine;
imidazole compounds, bifonazole, butoconazole, clotrimazole, econazole, fenticonazole, isoconazole, ketoconazole, miconazole, omoconazole, oxiconazole, sertaconazole, sulconazole, tioconazole;
triazole compounds, albaconazole, fluconazole, isavuconazole, itraconazole, posaconazole, ravuconazole, terconazole, voriconazole;
triazole compounds, abafungine;
allylamines, amorolfine, butenafine, naftifine, terbinafine;
echinocandins, anidulafungine, caspofungine, micafungine;
benzoic acid, cerulenin, ciclopirox, olamine, flucytosine, 5-fluorocytosine, griseofulvine, haloprogine, polygodial, tolnaftate, undecylenic acid, crystal violet;
chlorhexidine, polyvinylpyrrolidone (PVP) iodine, benzalkonium chloride, and chlorine.

18. The composition according to claim 7, wherein the composition is in the form of a tablet, coated tablet, gastro-resistant tablet, tablet, soft capsule, hard capsule, hard-shelled capsule; powder, pill, granule, solution, emulsion, suspension, syrup, eye drops, subgingival irrigation, mouth bath, chewing gum, toothpaste, patch, implant, suppository, paste, cream, gel, lotion, milk, ointment, spray, shampoo, varnish, plaster, catheter, compress, or gauze.

19. The composition according to claim 2, wherein the hydrophobic group is selected from:
a group with the formula —COR$^6$, wherein R$^6$ represents: (CH$_2$)$_{14}$—CH$_3$, —(CH$_2$)$_{16}$—CH$_3$, —(CH$_2$)$_7$—CH=CH—CH$_2$—(CH$_2$)$_7$—CH$_3$, —(CH$_2$)$_7$—CH=CH—(CH$_2$)$_7$—CH$_3$, and
poly(isobutylcyanoacrylate).

20. The composition according to claim 1, comprising:
(i) amphotericin B;
(ii) hydrophobised chitosan, wherein the hydrophobic group is poly(isobutylcyanoacrylate) (PIBCA); and
(iii) α-cyclodextrin.

* * * * *